(12) United States Patent
Nguyen et al.

(10) Patent No.: US 11,702,683 B2
(45) Date of Patent: Jul. 18, 2023

(54) DE NOVO POLYNUCLEOTIDE SYNTHESIS WITH SUBSTRATE-BOUND POLYMERASE

(71) Applicant: MICROSOFT TECHNOLOGY LICENSING, LLC, Redmond, WA (US)

(72) Inventors: Bichlien Nguyen, Seattle, WA (US); Jake Smith, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 322 days.

(21) Appl. No.: 16/886,638

(22) Filed: May 28, 2020

(65) Prior Publication Data

US 2021/0371891 A1    Dec. 2, 2021

(51) Int. Cl.
*C12P 19/34* (2006.01)
*B01J 19/00* (2006.01)

(52) U.S. Cl.
CPC ........... *C12P 19/34* (2013.01); *B01J 19/0046* (2013.01); *B01J 2219/00596* (2013.01); *B01J 2219/00722* (2013.01)

(58) Field of Classification Search
CPC ............. C12P 19/34; B01J 19/0046; B01J 2219/00596; B01J 2219/00722; C12Q 1/6844
See application file for complete search history.

(56) References Cited

U.S. PATENT DOCUMENTS

| | | |
|---|---|---|
| 7,494,797 B2 | 2/2009 | Mueller et al. |
| 8,323,939 B2 | 12/2012 | Hanzel et al. |

(Continued)

FOREIGN PATENT DOCUMENTS

| | | |
|---|---|---|
| WO | 2017142913 A1 | 8/2017 |
| WO | 2017156218 A1 | 9/2017 |

(Continued)

OTHER PUBLICATIONS

Bi, et al., "Building Addressable Libraries: The Use of "Safety-Catch" Linkers on Microelectrode Arrays", In Journal of the American Chemical Society vol. 132, Issue 49, Nov. 19, 2010, pp. 17405-17407.

(Continued)

*Primary Examiner* — Kyoung Lee
(74) *Attorney, Agent, or Firm* — Newport IP, LLC; Benjamin A. Keim

(57) ABSTRACT

De novo polynucleotide synthesis is performed with a substrate-bound polymerase. The polymerase is attached to a solid substrate such as a microelectrode array. The polymerase adds nucleotides to growing polynucleotides strands that are also attached to the solid substrate. Spatial control of polymerase activity is achieved by changing the rate of nucleotide polymerization at selected locations on the surface of the solid substrate. The rate of polymerization is changed by inhibiting or promoting activity of the polymerase. In some implementations, activation of electrodes in the microelectrode array changes the rate of nucleotide polymerization. Nucleotides are added to the growing polynucleotide strands at areas where the polymerase is active. By varying the locations where the substrate-bound polymerase is active and the species of nucleotide added, a population of polynucleotides with different, arbitrary sequences is synthesized on the surface of the solid substrate.

20 Claims, 6 Drawing Sheets

(56) References Cited

U.S. PATENT DOCUMENTS

| | | | |
|---|---|---|---|
| 10,059,929 | B2 | 8/2018 | Efcavitch et al. |
| 2006/0275927 | A1 | 12/2006 | Dubin et al. |
| 2015/0196917 | A1 | 7/2015 | Kay et al. |
| 2015/0203887 | A1 | 7/2015 | Lazinski et al. |
| 2018/0274001 | A1 | 9/2018 | Efcavitch et al. |
| 2019/0360013 | A1* | 11/2019 | Griswold, Jr. ....... C12N 9/1264 |
| 2020/0362394 | A1 | 11/2020 | Gawad et al. |
| 2021/0047669 | A1* | 2/2021 | Nguyen ............. C12Q 1/6874 |
| 2021/0071170 | A1 | 3/2021 | Nguyen et al. |

FOREIGN PATENT DOCUMENTS

| | | |
|---|---|---|
| WO | 2017176541 A1 | 10/2017 |
| WO | 2017196783 A1 | 11/2017 |
| WO | 2017223517 A1 | 12/2017 |
| WO | 2018119253 A1 | 6/2018 |
| WO | 2019079802 A1 | 4/2019 |
| WO | 2019222612 A1 | 11/2019 |
| WO | 2021034375 A1 | 2/2021 |

OTHER PUBLICATIONS

Chen, et al., "The History and Advances of Reversible Terminators Used in New Generations of Sequencing Technology", Published in Journal of Genomics, Proteomics & Bioinformatics, vol. 11, Issue 1, Feb. 2013, pp. 34-40.

Chiesi, et al., "The Use of Quench Reagents for Resolution of Single Transport Cycles in Sarcoplasmic Reticulum", Published in the Journal of Biological Chemistry, vol. 254, Issue 20, Oct. 25, 1979, pp. 10370-10377.

Egeland, et al., "Electrochemically Directed Synthesis of Oligonucleotides for DNA Microarray Fabrication", In Journal of Nucleic Acids Research, vol. 33, Issue 14, Aug. 5, 2005, pp. 1-7.

Hart, et al., "Synthesis and Characterization of trans-Dichlorotetrakis(imidazole)cobalt(III) Chloride: A New Cobalt(III) Coordination Complex With Potential Prodrug Properties", In Journal of Bioinorganic Chemistry and Applications, vol. 2018, Article ID 4560757, Sep. 3, 2018, 7 Pages.

Heffern, et al., "Cobalt Derivatives as Promising Therapeutic Agents", In Journal Current opinion in chemical biology, vol. 17, Issue 2, 2013, pp. 189-196.

Lee, et al., "Photon-directed Multiplexed Enzymatic DNA Synthesis for Molecular Digital Data Storage", In repository of bioRxiv, https://doi.org/10.1101/2020.02.19.956888, Feb. 20, 2020, pp. 1-24.

Williams, et al., "An Artificial Processivity Clamp Made with Streptavidin Facilitates Oriented Attachment of Polymerase-DNA Complexes to Surfaces", Published in Journal Nucleic Acids Research, vol. 36, Issue 18, Aug. 22, 2008, pp. 1-11.

Lee, et al., "Terminator-free Template-independent Enzymatic DNA Synthesis for Digital Information Storage", Published in Nature Communications, vol. 10, Article No. 2383, Jun. 3, 2019, pp. 1-12.

Motea, et al., "Terminal Deoxynucleotidyl Transferase: The Story of a Misguided DNA Polymerase", Published in Biochimica et Biophysica Acta (BBA)—Proteins and Proteomics, vol. 1804, Issue 5, May 2010, pp. 1151-1166.

Mukai, et al., "Sequential Reactions of Surface-Tethered Glycolytic Enzymes", Published in Journal of Chemistry & Biology, vol. 16, Issue 9, Sep. 25, 2009, pp. 1013-1020.

Shaw, et al., "Photoredox Catalysis in Organic Chemistry", In the Journal of Organic Chemistry, vol. 81, Issue 16, Aug. 1, 2016, pp. 6898-6926.

Yates, et al., "Methodologies for "Wiring" Redox Proteins/Enzymes to Electrode Surfaces", Published in Chemistry European Journal, vol. 24, Issue 47, Aug. 22, 2018, pp. 12164-12182.

Richey, et al., "Mg Anode Corrosion in Aqueous Electrolytes and Implications for Mg-Air Batteries", In Journal of The Electrochemical Society, vol. 163, Issue 6, 2016, pp. A958-A963.

Palluk, et al., "De novo DNA Synthesis Using Polymerasenucleotide Conjugates", Published in Nature Biotechnology vol. 36, Issue 7, Jul. 2018, 24 Pages.

Zou, et al., "Investigating the Effect of Two-Point Surface Attachment on Enzyme Stability and Activity" In Journal of the American Chemical Society vol. 140, Issue 48, Nov. 7, 2018, pp. 16560-16569.

Nguyen, et al., "Microelectrode Arrays: A General Strategy for Using Oxidation Reactions To Site Selectively Modify Electrode Surfaces", In Journal of Langmuir vol. 30, Issue 8, Feb. 5, 2014, pp. 2280-2286.

"International Search Report and Written Opinion Issued in PCT Application No. PCT/US20/037104", dated Sep. 28, 2020, 10 Pages.

"International Search Report and Written Opinion Issued in PCT Application No. PCT/US21/028273", dated Aug. 27, 2021, 11 Pages.

Nguyen, et al., "Long-Term Stability and Integrity of Plasmid-Based DNA Data Storage", In Journal of Polymers, vol. 10, Issue 1, Jan. 1, 2018, 10 Pages.

Organick, et al., "Random Access in Large-Scale DNA Data Storage", In The Journal of Nature Biotechnology, vol. 36, Issue No. 3, Mar. 2018, pp. 242-248.

"International Search Report and Written Opinion Issued in PCT Application No. PCT/US20/038020", dated Sep. 21, 2020, 12 Pages.

"Non Final Office Action Issued in U.S. Appl. No. 16/563,797", dated Jan. 18, 2022,22 Pages.

Hoang, et al., "Modification of 3' Terminal Ends of DNA and RNA Using DNA Polymerase 9 Terminal Transferase Activity", In Journal of Bio-Protocol, vol. 7, Issue 12, Jun. 20, 2017, pp. 1-9.

Vortler, et al., "tRNA-Nucleotidyltransferases: Highly Unusual RNA Polymerases with Vital Functions", In Journal of FEBS Letters, vol. 584, Issue 2, Jan. 21, 2010, pp. 297-302.

Thomas, et al., "One-Step Enzymatic Modification of RNA 3' Termini using Polymerase θ", In Journal of Nucleic Acids Research, vol. 47, Issue 7, Mar. 1, 2019, pp. 3272-3283.

"Non Final Office Action Issued in U.S. Appl. No. 16/543,433", dated May 27, 2022, 9 Pages.

"Final Office Action Issued in U.S. Appl. No. 16/563,797", dated Jun. 27, 2022, 22 Pages.

2021-0047669-A1, filed Feb. 18, 2021.

20210071170, filed Mar. 11, 2021.

"Notice of Allowance Issued in U.S. Appl. No. 16/543,433", dated Apr. 14, 2023, 6 Pages.

"Notice of Allowance Issued in U.S. Appl. No. 16/543,433", dated Mar. 29, 2023, 7 Pages.

\* cited by examiner

DE NOVO POLYNUCLEOTIDE SYNTHESIS WITH SUBSTRATE-BOUND POLYMERASE

BACKGROUND

There are multiple techniques for synthesizing polynucleotides such as the nucleoside phosphoramidite method and enzymatic polynucleotide synthesis. The nucleoside phosphoramidite method uses chemicals to build polynucleotide strands from phosphoramidite reagents. Enzymatic polynucleotide synthesis uses template-independent polymerases, such as terminal deoxynucleotide transferase (TdT), to add nucleotides onto growing polymerase strands. Both techniques may be used for solid-phase polynucleotide synthesis in which the growing polynucleotide strands are anchored to a solid substrate such as a bead or an array.

One emerging use of synthetic polynucleotides is for storage of digital data. Deoxyribonucleic acid (DNA) provides a high storage density and, if maintained in proper conditions, may be stable for hundreds of years. However, using DNA as a medium for data storage requires synthesis of a large number of polynucleotides with specific sequences.

Current polynucleotide synthesis techniques each have advantages and disadvantages. Additional techniques for highly parallel and automated polynucleotide synthesis will have many uses including in DNA data storage applications. This disclosure is made with respect to these and other considerations.

SUMMARY

This disclosure provides devices, methods, and systems for using solid substrates with tethered polymerases for de novo synthesis of polynucleotides. A polymerase is an enzyme that catalyzes the addition of nucleotide monomers onto a growing polynucleotide strand. In some implementations, the polymerase is TdT. The polymerase may be attached directly to the surface of a solid substrate or attached via a linker molecule. The substrate may be an inert surface such as silicon dioxide, glass, or a metal. In some implementations the solid substrate may be a microelectrode array with multiple, individually-addressable electrodes.

Polynucleotide strands are also attached to the surface of the solid substrate. Polymerization activity of a polymerase extends the polynucleotide strands by addition of free nucleotides. Each polymerase bound to the surface of the solid substrate is able to add nucleotides onto nearby polynucleotides. Because both the polymerases and the polynucleotides are attached to the solid substrate, the area of effect for each polymerase is limited.

Spatial addressability, the ability to turn polymerization "on" or "off" at selected locations on the solid substrate, enables the synthesis of polynucleotides of different sequences. Selected locations on the surface of the solid substrate are "activated," a single species of nucleotide is provided, and that nucleotide is incorporated into the growing polynucleotide strands only at those locations. Nucleotide addition does not occur at locations that are not "activated." Activation may be achieved by activating the polymerases (e.g., providing a necessary cofactor or otherwise making the polymerases available to interact with the polynucleotides). Activation may also be achieved by removing blocking groups from the polynucleotides that prevent incorporation of additional nucleotides. The selected locations and the selected nucleotide species may both be independently changed in subsequent rounds of addition. With this technique polynucleotides with different, arbitrary sequences are synthesized on the surface of the solid substrate.

A system for de novo synthesis of polynucleotides includes a solid substrate with polymerases and polynucleotides tethered to its surface. The system includes components for changing the rate of nucleotide polymerization on selected locations on the surface of the solid substrate. If nucleotide polymerization is promoted (or alternatively not inhibited) at specific locations, polymerization will occur at those locations but not others. There are multiple techniques and devices that may be used to affect the rate of nucleotide polymerization. For example, the solid substrate may be a microelectrode array and activation of specific electrodes in the microelectrode array may affect the rate of nucleotide polymerization. Optoelectronics such as a photomask or a digital micromirror device may be used to direct light onto selected locations on the surface of the solid substrate. The light may cause a change in the rate of polymerization. A heater may elevate the temperature at selected locations on the solid substrate and change the rate of nucleotide polymerization. A targeted fluid deposition instrument (e.g., a chemical inkjet printer) may be used to precisely apply small volumes of reagents to the surface of the solid substrate. The reagents may promote or inhibit polymerization.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and not necessarily drawn to scale.

DETAILED DESCRIPTION

Figure 1:
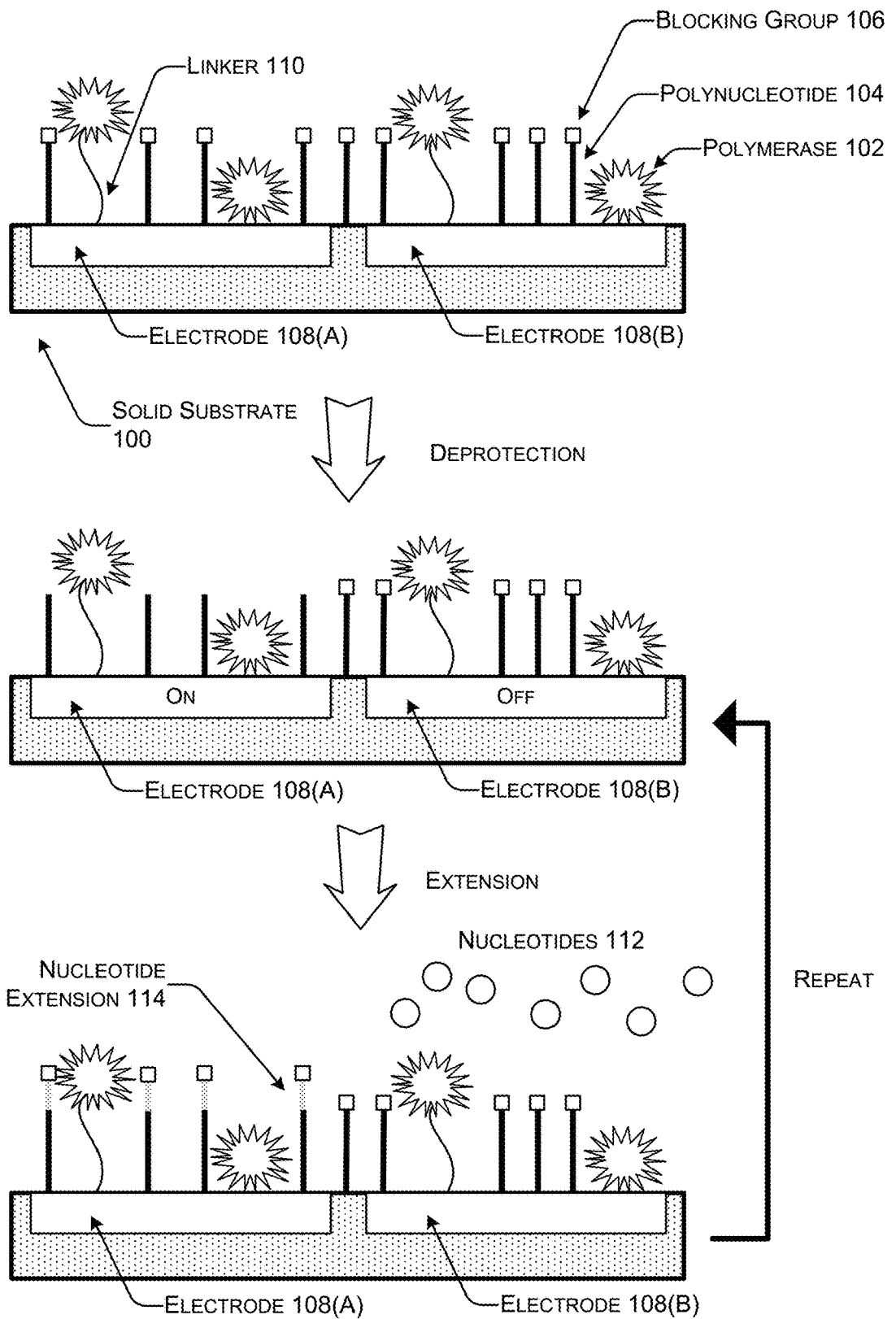
FIG. 1 is a diagram of polynucleotide synthesis with surface-bound polymerases on a solid substrate in which spatial addressability is achieved by deprotection of polynucleotides through the removal of blocking groups.

This disclosure provides techniques for solid-phase de novo synthesis of polynucleotides with any arbitrary sequence in which both the growing polynucleotide strands and the polymerases are attached to a solid substrate. Existing techniques for polynucleotide synthesis do not use substrate-bound polymerases. Polymerases that are free in solution are removed with each wash step resulting in higher reagent costs. Polymerases tethered to a solid substrate may be reused. Also, because substrate-bound polymerases do not move, the precision of spatial addressability may increase for implementations in which polymerization is controlled by enzyme activation. Without being bound by theory, it is believed that tethering the polymerase to the solid substrate together with the growing polynucleotide strands increases the effective concentration of the polymerase and thus the rate of the polymerization reaction.

There are many uses for synthetic polynucleotides having specified sequences such as basic research, medicine, and nanoengineering (e.g., DNA origami). One relatively recent application for synthetic polynucleotides is digital data storage. Polynucleotides such as DNA may be used to store digital information by designing a sequence of nucleotide bases that encodes the zeros and ones of the digital information. There are various techniques and encoding schemes known to those of skill in the art for using nucleotide bases to represent digital information. See Lee Organick et al., *Random Access in Large-Scale DNA Data Storage*, 36:3 Nat. Biotech. 243 (2018) and Melpomeni Dimpoulou et al., *Storing Digital Data Into DNA: A Comparative Study of Quaternary Code Construction*, ICASSP Barcelona, Spain (2020). Advantages of using polynucleotides rather than another storage media for storing digital information include information density and longevity. The sequence of nucleotide bases is designed on a computer and then polynucleotides with those sequences are synthesized. The polynucleotides may be stored and later read by a polynucleotide sequencer to retrieve the digital information.

Polynucleotides, also referred to as oligonucleotides, include both DNA, ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases. Nucleotides include both deoxyribonucleotides and ribonucleotides covalently linked to one or more phosphate groups.

Polymerases include template-dependent polymerases and template-independent polymerases. All polymerase are enzymes that synthesize DNA from deoxyribonucleotides or RNA from ribonucleotides. A polymerase can add free nucleotides to the 3' end of a newly forming strand. This results in elongation of the newly forming strand in a 5'-3' direction. No known polymerase can begin a new chain. Polymerases can only add a nucleotide onto a pre-existing 3'-OH group, and therefore use a primer or initiator to which the first nucleotide is added.

Polymerases require a divalent metal cofactor to catalyze polymerization of nucleotides. A cofactor is a non-protein chemical compound or metallic ion that is required for an enzyme's activity as a catalyst. DNA and RNA polymerases, including the template-independent polymerase TdT, require a divalent metal cofactor cation to catalyze the polymerization of individual nucleotides into a polynucleotide. Absent the metal cofactor in the proper oxidation state of +2, polymerization will not occur at an appreciable rate even if all other necessary components are present. Regulation of the oxidation state of the metal cofactor is controlled by redox reactions initiated through electrodes or addition of chemical redox reagents.

Template-dependent polymerases, also called DNA-dependent DNA polymerases, require a template strand with an attached primer to initiate synthesis. There are many commercially available template-dependent polymerases known to those of ordinary skill in the art. Examples of template-dependent polymerases include *E. coli* DNA polymerase I and its Klenow fragment, T4 DNA polymerase, native and modified T7 DNA polymerase, phi29 DNA polymerase, Bst DNA polymerase, and Taq DNA polymerase, Deep Vent® DNA Polymerase (available from New England Biolabs, Inc.), Q5® high-fidelity DNA polymerase (available from New England Biolabs, Inc.), and KAPA HiFi DNA polymerase (available from Roche Diagnostics). Characteristics and reaction conditions of the template-dependent polymerases are known to those of skill in the art and are available from the supplier and/or presented in reference material such as Kucera, R. B. and Nichols, N. M., *DNA-Dependent DNA Polymerases,* 84 Current Protocols in Molecular Biology, 3.5.1-3.5.19 (2008). Techniques exist for using template-dependent polymers for de novo synthesis of polynucleotides. One such technique uses rolling templates that successively direct the addition of one or more nucleotides to a relatively longer polynucleotide primer strand. See U.S. Pat. No. 6,136,568. A similar technique, synthesis of single-stranded polynucleotides on a solid surface using transient hybridization and extension by DNA polymerases is discussed in Kendall Hoff et al., *Enzymatic Synthesis of Designer DNA Using Cyclic Reversible Termination and a Universal Template,* 9(2) ACS Synth. Biol. 283 (2020).

Template-independent polymerases are DNA or RNA polymerases that perform de novo oligonucleotide synthesis without the use of a template strand. Currently known template-independent polymerases include TdT and tRNA nucleotidyltransferase. TdT includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template-independent polymerase as used herein includes full-length wild-type, truncated, or otherwise modified TdT or tRNA nucleotidyltransferase, and any subsequently discovered or engineered polymerases that can perform template-independent synthesis of polynucleotides. Template-independent polymerase as used herein does not encompass modifications of TdT or tRNA nucleotidyltransferase that render those enzymes incapable of performing template-independent nucleotide polymerization.

TdT is a protein that evolved to rapidly catalyze the linkage of naturally occurring deoxynucleotide triphosphates (dNTPs). TdT adds nucleotides indiscriminately to the 3' hydroxyl group at the 3' end of single-stranded DNA. TdT performs unregulated synthesis adding any available dNTP. TdT uses an existing single-stranded polynucleotide referred to as an "initiator" as the starting point for synthesis. Initiators as short as three nucleotides have been successfully used with TdT for enzymatic synthesis of DNA. Suitable initiator length ranges from three nucleotides to about 30 nucleotides or longer. During the polymerization, the template-independent polymerase holds a single-stranded DNA strand (which initially is only the initiator) and adds dNTPs in a 5'-3' direction. TdT activity is maximized at approximately 37° C. and performs enzymatic reactions in an aqueous environment.

Because TdT performs unregulated synthesis, using this enzyme to create a polynucleotide with a pre-specified arbitrary sequence requires regulation and control of the TdT activity. One technique to regulate TdT activity is limiting the available nucleotides to only a single type of dNTP or NTP (e.g., only dATP, dCTP, dGTP, dTTP, or UTP). Thus, providing only one choice forces the enzyme to add that type of nucleotide. However, this does not prevent the TdT from adding that nucleotide multiple times thereby creating homopolymers. Techniques for limiting homopolymer creation by TdT include using nucleotides with removable blocking groups, covalently coupling individual nucleotides to TdT enzymes, and limiting the available quantity of nucleotides. Examples of these techniques are briefly described below.

One technique for controlling enzymatic synthesis of oligonucleotides with TdT uses a modified TdT enzyme and dNTP analogs with blocking groups to prevent unregulated nucleotide addition. An example of this technique is described in U.S. Pat. No. 10,059,929. Techniques for enzymatic polynucleotide synthesis that use blocking groups typically flood a reaction tube with only one type of dNTP. The blocking group prevents polymerization so only a single nucleotide is added to the growing polynucleotide strand. Once coupling has taken place, the free dNTPs are washed away, the blocking group is removed with a deblocking solution, and the system is primed for the next round of single-nucleotide addition.

Another technique for enzymatic synthesis uses TdT enzymes each tethered to a single dNTP by a cleavable linker. See Sebastian Palluk et al., De novo *DNA synthesis using polymerase-nucleotide conjugates,* 36(7) Nature Biotechnology 645 (2018) and WO 2017/223517 A1. In this system, the TdT acts as its own blocking group preventing further chain elongation.

A third technique for nucleotide synthesis using TdT regulates activity of the polymerase by including the enzyme apyrase, which degrades nucleoside triphosphates into their TdT-inactive diphosphate and monophosphate precursors. In this technique, apyrase limits polymerization by competing with TdT for nucleoside triphosphates. See Henry H. Lee et al., *Terminator free template-independent Enzymatic DNA Synthesis for Digital Information Storage,* 10:2383 Nat. Comm. (2019) and WO 2017/176541 A1.

Spatial control of TdT synthesis using enzymes free in solution and anchored polynucleotide strands has been achieved by limiting availability of metal cofactors. In one implementation, the metal cofactors may be kept in an inactive state by caging with DMNP-EDTA and released at specific locations by exposure to patterned UV light. Diffusion of the metal cofactors is controlled by providing an excess of the caging molecules. The TdT and nucleotides are provided in a standard synthesis master mix. See Howon Lee et al., *Photon-directed Multiplexed Enzymatic DNA Synthesis for Molecular Digital Data Storage,* bioRxiv 2020.02.19.956888.

In another implementation, the oxidation state of metal cofactors are toggled between +2 (active) and +1 or +3 (inactive). Spatial control of the oxidation state is achieved by activation of electrodes on a microelectrode array, controlled addition of redox reagents, or other techniques. Diffusion of the metal cofactors in the +2 oxidation state is controlled by providing scavenger molecules that either change the oxidation state or sequester the metal cofactors. See U.S. patent application Ser. No. 16/543,433 filed on Aug. 16, 2019 with the title "Regulation of Polymerase Using Cofactor Oxidation States." However, in both of these techniques active TdT enzymes complexed to metal cofactors in the +2 oxidation state are free to diffuse across the surface of the solid substrate.

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual,* Cold Spring Harbor Laboratory Press, $4^{th}$ ed. (2012).

FIG. 1 shows a solid substrate 100 covered with surface-bound polymerases 102 and polynucleotides 104 on which spatial control of polymerase activity is regulated by removal of blocking groups 106 on the ends of the polynucleotides 104. The solid substrate 100 may be made of any material that is capable of anchoring polynucleotides 104 and polymerases 102. For example, the solid substrate 100 may be formed from silicon dioxide, glass, an insoluble polymer, a non-reactive metal such as gold, silver, or platinum, or other material.

The solid substrate 100 is an example of is a platform used for solid-phase synthesis. Solid-phase synthesis is a method in which molecules are covalently bound on a solid support material and synthesized step-by-step in a single reaction vessel. Solid-phase synthesis may be used to make many types of polymers including, but not limited to, polynucleotides 104.

In some implementations, the solid substrate 100 may be or may include a microelectrode array with a plurality of electrodes 108. For simplicity, only two electrodes 108(A), 108(B) are illustrated, but it is to be understood that the microelectrode array may include more electrodes. The electrodes 108 may be formed from a metal such as gold or another metal plated with gold. The polymerases 102, and the polynucleotides 104, may be attached to the electrodes 108 as well as to areas on the surface of a microelectrode array that do not contain an electrode 108.

The electrodes 108 may be implemented with any known technology for creating microelectrodes such as complementary metal-oxide-semiconductor (CMOS) technology. CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the microelectrode array. Each electrode 108 in the microelectrode in the array may be independently addressed allowing the creation of arbitrary and variable voltage microenvironments across the surface of the microelectrode array.

High microelectrode density allows for fine-scale level control of the ionic environment at the surface of the microelectrode array. A microelectrode array may have a microelectrode density of approximately 1024 microelectrodes/$cm^2$, approximately 12,544 microelectrodes/$cm^2$, or a different density. Examples of microelectrode arrays are provided in Bo Bi et al., *Building Addressable Libraries: The Use of "Safety-Catch" Linkers on Microelectrode Arrays,* 132 J. Am. Chem. Soc. 17,405 (2010), Bichlien H. Nguyen et al., *Microelectrode Arrays: A General Strategy for Using Oxidation Reactions To Site Selectively Modify Electrode Surfaces,* 30 Langmuir 2280 (2014), and U.S. patent application Ser. No. 16/435,363 filed on Jun. 7, 2019, with the title "Reversing Bias in Polymer Synthesis Electrode Array." One example of a microelectrode array and techniques for attaching polynucleotides to the surface of the array is provided in a Ryan D. Egeland & Edwin M. Southern, *Electrochemically Directed Synthesis of Oligonucleotides for DNA Microarray Fabrication*, 33(14) Nucleic Acids Res. e125 (2005).

The polynucleotides 104 may be attached to the solid substrate 100 by any known or later developed technique for anchoring single-stranded DNA or RNA to a solid support. Suitable techniques include those used in conventional solid-phase synthesis of oligonucleotides or for the creation of DNA microarrays. In some implementations, the surface of the solid substrate 100 may be functionalized and the polynucleotides 104 may be attached to the functional groups rather than directly to the molecules of the solid substrate 100. Initiator sequences may be attached or synthesized onto the surface of the solid substrate 100 to provide a starting sequence for polymerases 102 to extend.

Each of the initiators attached to the solid substrate 100 may have the same nucleotide sequence or one or more of the initiators may have different sequences. The sequence of any one or more of the initiators may be a random sequence of nucleotides. The initiators may be attached to the solid substrate 100 before, after, or concurrently with attachment of the polymerase 102 by any known technique for attaching single-stranded polynucleotides 104 to a solid support. The length of an initiator may be about 3-30 nucleotides, about 15-25 nucleotides, or about 20 nucleotides.

The polymerases 102 can be anchored directly to the solid substrate 100 through the sidechain of an amino acid such as cysteine. One example of directly attaching an enzyme to a solid surface uses enzyme variants containing cysteinyl residues that are immobilized on maleimide-terminated self-assembled monolayer (SAM) surfaces. See Xingquan Zou et al., *Investigating the Effect of Two-Point Surface Attachment on Enzyme Stability and Activity*, 140 (48) J. Am. Chem. Soc. 16560 (2018).

The polymerases 102 can be anchored to the solid substrate 100 via a linker 110. The linker 110 is a molecule that connects the polymerase 102 to the solid substrate 100. The linker 110 may be any non-reactive entity with functionality for attachment to both the polymerase 102 and the solid substrate 100. For example, TdT has been successfully attached to a poly(ethylene glycol) (PEG) linker which in turn was attached to a single nucleotide. See Palluk supra. The length of the linker 110 influences the range of polymerase activity. A polymerase 102 attached to a longer linker 110 will generally be able to interact with polynucleotides 104 over a larger area of the solid substrate 100 than one attached to a shorter linker 110. Some examples of suitable linkers 110 include PEG, alkyl chains, peptides, biotin-streptavidin linkages, and cross-linked enzyme aggregates (CELA). See Ahmad Abolpour Homaei et al., *Enzyme immobilization: an update*, 6(4) J. Chem. Biol. 185 (2013) for a discussion of CELA and other techniques for attaching enzymes to solid supports.

There are multiple and varied techniques for attaching enzymes, such as polymerases, to solid substrates. Enzymes have been successfully attached to nickel-nitrilotriacetic acid modified surface by modifying the enzymes to have a hexahistidine (His-) tag at the amino terminus. See Chinatsu Mukai et al., *Sequential Reactions of Surface-Tethered Glycolytic Enzymes*, 16(9) Chemistry & Biology 1013 (2009). The Therminator™ variant of 9° N DNA polymerase has been immobilized on a solid support by modifying the enzyme with biotinylated peptides. The tetravalent binding capacity of streptavidin and its strong affinity for biotin to is used to anchor the enzyme to a glass surface also coated with biotin. See John G. K. Williams et al., *An artificial processivity clamp made with streptavidin facilitates oriented attachment of polymerase-DNA complexes to surfaces*, 36(18) Nucleic Acids Research e121 (2008). Other types of anchoring techniques for enzymes using amine-carboxylic acid equivalent bonds and amine-aldehyde bonds are described in Nicholas D. J. Yates, *Methodologies for "Wiring" Redox Proteins/Enzymes to Electrode Surfaces*, 24(47) Chemistry A European Journal 12164 (2018). U.S. Pat. No. 8,323,939 describes modified polymerases that include surface coupling domains such as an added recombinant dimer domain of the enzyme, a large extraneous polypeptide domain, a polyhistidine tag, a HIS-6 tag, a His-10 tag, biotin, an avidin sequence, a GST sequence, glutathione, a BiTag (AviTag) sequence, an S tag, a SNAP-tag, an antibody, an antibody domain, an antibody fragment, an antigen, a receptor, a receptor domain, a receptor fragment, a ligand, a dye, an acceptor, and a quencher.

The blocking groups 106 on the ends of the polynucleotides 104 prevent extension of the polynucleotides 104. The blocking groups 106 may be located on the 3'-end of the polynucleotides 104. Removal of a 3' blocking group 106 replaces the blocking group 106 with a 3' hydroxyl group. Any type of known or later developed blocking group 106 may be used.

Some examples of blocking group 106 include esters, ethers, carbonitriles, phosphates, carbonates, carbamates, hydroxylamine, borates, nitrates, sugars, phosphoramide, phosphoramidates, phenylsulfenates, sulfates, sulfones, and amino acids. See Michael L. Metzker et al., *Termination of DNA Synthesis by Novel 3'-modified-deoxyribonucleoside 5'-triphosphates*, 22(20) Nucl. Acids Res., 4259 (1994) and U.S. Pat. Nos. 5,763,594, 6,232,465, 7,414,116, and 7,279,563. Other types of blocking groups include 3'-O-amino, 3'-O-allyl, and a 3'-O-azidomethyl groups. Further examples of specific blocking groups include O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetra-hydrofuranyl; O-[2-methyl,4-methoxy]-tetrahydropyranyl; O-[5-methyl]-tetrahydropyranyl; and O-tetrahydrothiofuranyl. See U.S. Pat. No. 8,133,669 for a discussion of these blocking groups. Additional examples of blocking groups are provided in U.S. patent application Ser. No. 16/230,787 filed on Dec. 21, 2018.

Suitable 3' blocking groups 106 and methods for removing the 3' blocking groups 106 include, but are not limited to, terminators used in next generation sequencing such as those described in Fei Chen et. al., *The History and Advances of Reversible Terminators Used in New Generations of Sequencing Technology*, 11 Genomics Proteomics Bioinformatics 34 (2013). Additional examples of suitable 3' blocking groups 106 and methods for use are described in U.S. Pat. No. 7,541,444.

The blocking groups 106 may be photolabile. Photolabile blocking groups are removed by exposure to a specific wavelength of light. There are a large number of known types of photo-cleavable linkers that can attach blocking groups 106. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain. Amine-to-thiol bonds may be cleaved by ultraviolet (UV) light with a wavelength of about 365-405 nm. One example of a photocleavable blocking group is the "virtual terminator" described in Jayson Bowers et al., *Virtual terminator nucleotides for next-generation DNA sequencing*, 6(8) Nat Methods 593 (2009).

The blocking groups 106 may be thermolabile blocking groups that are removed by heat in the absence of enzymes, chemical reagents, and the like. Examples of thermolabile blocking groups include those described in U.S. Pat. Pub. Nos. 2010/0003724 and 2007/0281308.

If the solid substrate 100 is a microelectrode array, blocking groups 106 that are cleaved or removed by a change in the ionic environment may be suitable. For example, blocking groups 106 may be connected to the polynucleotides 104 by electrochemically-cleavable linkers. Electrochemically-cleavable linkers may be cleaved thereby releasing a blocking group 106 by activation of an electrode 108. Examples of electrochemically-cleavable linkers are provided in U.S. patent application Ser. No. 16/781,987 filed on Feb. 4, 2020 and entitled "Electrochemically-cleavable Linkers." In an implementation, the blocking groups 106 may be removed by redox reactions. Examples of redox-cleavable 3' blocking groups include hydroxylamine and azidomethyl groups. The allyl blocking group is cleavable by $Pd_0$. Redox reactions may be initiated by activation of individual electrodes 108 of the microelectrode array.

The blocking groups 106 are removed from some portion of the surface of the solid substrate 100. This deprotects those polynucleotides 104 from which the blocking groups 106 were removed. The blocking groups 106 may be removed by any of the techniques discussed above. In some implementations, the blocking groups are selectively removed by activation of one electrode 108(A) while another electrode 108(B) is not activated.

The surface of the solid substrate 100 may be flooded or covered with nucleotides 112. A nucleotide is a nucleoside linked to one or more phosphate groups. In some implementations, a nucleotide 112 may be a deoxynucleoside triphosphate (dNTP) or a ribose triphosphate (NTP). The nucleotides 112 may be limited to only a single species of nucleotide (e.g., only A, G, C, or U/T) so that the same nucleotide is added at all of the polynucleotides 104 where the blocking group 106 is removed. Depending on the structure of the nucleotide 112 and/or the reaction conditions, the nucleotide 112 incorporates once or multiple times at locations on the solid substrate 100 without blocking groups 106 such as the activated electrode 108(A). The nucleotide 112 may include a blocking group 106 so that incorporation of a nucleotide 112 adds a new blocking group extends and re-blocks a polynucleotide 104.

The nucleotides 112 and other entities that are not attached to the solid substrate 100 are present in an aqueous solution (not shown) that covers the surface of the solid substrate 100. The aqueous solution may include buffers, salts, electrolytes, and the like. The polymerases 102 add the nucleotides 112 on the end of the unblocked polynucleotides 104. This creates a nucleotide extension 114 that elongates the polynucleotides 104 attached to the solid substrate 100 by addition of one or more of the nucleotides 112. If the nucleotides 112 include blocking groups 106 this also re-blocks the polynucleotides 104.

In this example, the nucleotide extension 114 is present only on the electrode 108(A) that was activated and not on the other electrode 108(B) that was not activated. This creates spatial addressability on the surface of the solid substrate 100 which allows for control of where nucleotides 112 are added to growing polynucleotides 104. Repeated rounds of deprotection and extension allow for the synthesis of polynucleotides 104 with different sequences. Nucleotides 112 that remain in solution may be removed by a wash step between rounds.

Figure 2:
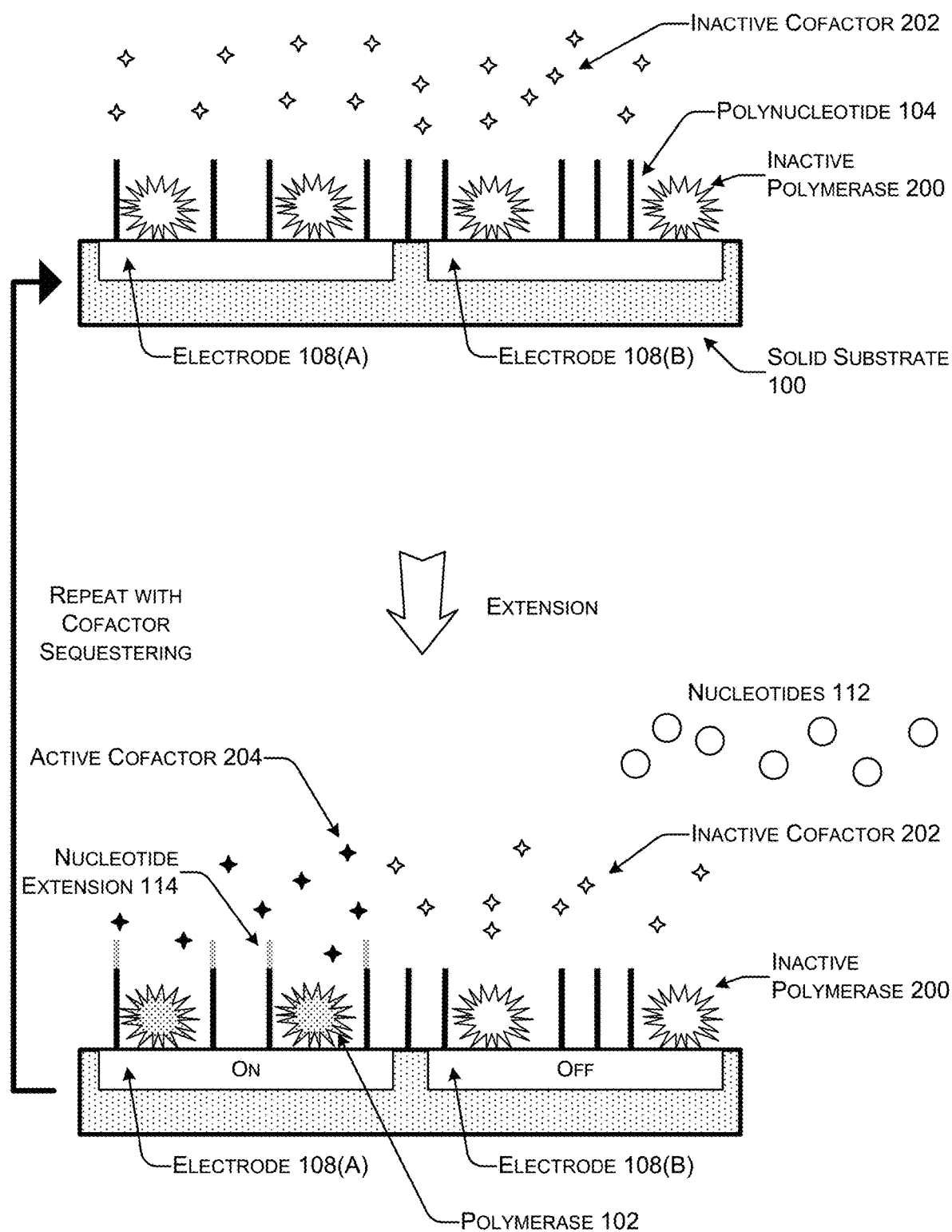
FIG. 2 is a diagram of polynucleotide synthesis with surface-bound polymerases on a solid substrate in which spatial addressability is achieved by changing the oxidation state of a metal cofactor.

FIG. 2 shows spatial control of polymerase 102 activity by regulation of enzyme cofactor oxidation states. In this implementation, the surface of a solid substrate 100 is also coated with polymerases 102 and polynucleotides 104 as shown in FIG. 1. However, spatial control in FIG. 2 is achieved by regulation of cofactor oxidation states rather than through selective removal of blocking groups 106 as shown in FIG. 1. Thus, the polynucleotides 104 in this implementation may or may not include blocking groups 106.

The polymerases 102 are inactive polymerases 200 when the available metal cofactors are inactive cofactors 202. An inactive cofactor 202 is a metal cofactor with an oxidation state that does not allow for specific ligand coordination of the polymerase 102 around the metal cofactor. For many polymerases, the oxidation state that allows for ligand coordination is +2. When the oxidation state is not +2, polymerases cannot coordinate with the cation and the nucleotide polymerization reaction is stopped. Polymerase activity can be controlled by introducing the metal cofactor an oxidation state other than the +2 oxidation state then changing the oxidation state of the metal cofactor to the +2 oxidation state. This change in metal cofactor oxidation state converts inactive polymerases 200 to polymerases 102 that are active.

An aqueous solution that covers the surface of the solid substrate 100 may initially include only inactive cofactors 202. This prevents polynucleotide extension from occurring anywhere on the surface of the solid substrate 100. Spatial control of the metal cofactor oxidation state enables addressable activation of inactive polymerase 200, and thus, spatial control of the locations on the solid substrate 100 at which polynucleotide synthesis proceeds.

The substrate independent polymerase TdT, for example, uses divalent metal cofactor cations for catalysis. TdT is able to use a variety of divalent metal cations such as $Co^{2+}$, $Mn^{2+}$, $Zn^{2+}$, and $Mg^{2+}$. The metal cofactors may be provided in the forms of salts such as $MgCl_2$ or $CoCl_2$. The salts form hydrates such as $MgCl_2(H_2O)_x$ or $CoCl_2 \cdot nH_2O$ (n=1, 2, 6, and 9) in aqueous solution. The divalent metal cation coordinates with TdT and the triphosphate of a dNTP to catalyze the addition of a nucleotide 112 to the 3' terminal nucleotide on the end of a polynucleotide 104. This reaction creates a phosphodiester linkage between the nucleotide 112 and the polynucleotide 104 and releases pyrophosphate (PPi).

A first oxidation state is referred to as an "inactive" oxidation state resulting in an inactive cofactor 202. For TdT, the inactive oxidation state may be any oxidation state other than the +2 oxidation state such as 0 (solid metal), +1, +3, +4, etc. These oxidation states are referred to as inactive because the inactive polymerase 200 does not coordinate with the metal cofactor when its oxidation state is not +2. A second oxidation state for the metal cofactor is referred to as an "active" oxidation state in which the metal cofactor is an active cofactor 204 that has a +2 oxidation state. The +2 oxidation state is referred to as active because the polymerase can actively catalyze nucleotide polymerization when the metal cofactor has this oxidation state.

One suitable metal cofactor is cobalt. Cobalt can be provided as a cobalt complex such as a cobalt (III) complex or a cobalt (I) complex. Example cobalt complexes include trans-Dichlorobis(ethylenediamine)cobalt(III) chloride, pentaamminechlorocobalt(III) chloride, hexammine cobalt (III) chloride, trans-dichlorotetrakis(imidazole)cobalt(III) chloride or chlorotris(triphenylphosphine)cobalt(I). Synthesis of trans-Dichlorobis(ethylenediamine) cobalt (III) chloride, solubility in aqueous solutions, and reduction to cobalt (II) is described in Hart et al., *Synthesis and Characterization of trans-Dichlorotetrakis (imidazole)cobalt(III) Chloride: A New Cobalt(III) Coordination Complex with Potential Prodrug Properties*, Bioinorganic Chem. and Applications, vol. 2018, Article ID 4560757, (2018).

The cobalt complex may be reduced or oxidized to cobalt(II) chloride ($CoCl_2$). For example, a Co(III)-complex can be reduced to a Co(II)-complex which can undergo ligand exchange with a buffered aqueous solution to form Co(II) which can then coordinate with TdT to "activate" it for polynucleotide synthesis. A ligand exchange reaction involves the substitution of one or more ligands in a complex ion with one or more different ligands.

Another suitable metal cofactor is magnesium. Magnesium may also be present as a magnesium salt such as magnesium chloride ($MgCl_2$). Magnesium may be provided as metallic magnesium, Mg(0), and can be oxidized by electrolysis at an anode in buffered solution to generate Mg(II). Reversing the current direction can reduce the Mg(II) to Mg(0). One technique for obtaining Mg(II) from a magnesium anode is described in Francis W. Ritchey et al., *Mg Anode Corrosion in Aqueous Electrolytes and Implications for Mg-Air Batteries,* 163(6) J. Electrochemical Soc'y, A958 (2016).

The metal cofactor is converted between the inactive oxidation state and the active oxidation state by a redox reaction. Redox, short for reduction-oxidation reaction, is a type of chemical reaction in which the oxidation states of atoms are changed. Redox reactions are characterized by the transfer of electrons between chemical species, most often with one species (the reducing agent) undergoing oxidation (losing electrons) while another species (the oxidizing agent) undergoes reduction (gains electrons). The chemical species from which the electron is stripped is said to have been oxidized, while the chemical species to which the electron is added is said to have been reduced.

If the solid substrate 100 is a microelectrode array, the redox reaction may be initiated by an electrode 108. The redox reaction may be initiated directly or indirectly at the electrode surface. At the electrode surface, reduction or oxidation takes place using electron transfer directly at the electrode or mediated by the redox of a mediator. Redox mediators are chemicals with electrochemical activity. In a bioelectrocatalysis process, mediators may exchange electrons with fuels or oxidants at the reaction sites of the biocatalysts, and then diffuse to the surface of electrode and exchange electrons there. Use of mediators may also reduce the required electrode potential which in turn reduces the energy needed to change the metal cofactor into the active oxidation state. Mediators may be present in the aqueous solution that covers the solid substrate 100.

The aqueous solution that covers the solid substrate 100 may also include supporting electrolytes. A supporting electrolyte, in electrochemistry, is an electrolyte containing chemical species that are not electroactive (within the range of potentials used) and which has an ionic strength and conductivity much larger than those due to the electroactive species added to the electrolyte. Supporting electrolytes are also referred to as inert electrolytes or inactive electrolytes. In some implementations, PBS functions as the supporting electrolyte. Other types of salt solutions used in aqueous buffers for biological reactions may also function as the supporting electrolyte.

Location-specific control of cofactor oxidation states may also be achieved without a microelectrode array. For example, chemical redox reagents may be used to change the oxidation state of the metal cofactor from an inactive cofactor 202 to an active cofactor 204. The chemical redox reagents may be applied to selected locations on the solid substrate 100 by target fluid deposition. The chemical redox reagents contribute or receive electrons from the metal cofactor in the inactive oxidation state changing it to the active oxidation state such as $Mg^{2+}$ or $Co^{2+}$. For example, ascorbic acid is a reducing agent that can reduce cobalt(III) to cobalt(II). Cobalt(II) may be oxidized to cobalt(III) by an amine (e.g., ammonia, ethylenediamine, ethylenediaminetetraacetic acid (EDTA), or tris(hydroxymethyl) aminomethane) in the presence of oxygen. The oxygen may be present as dissolved atmospheric oxygen in the aqueous solution or may be provided such as the addition of hydrogen peroxide.

As a further example, the conversion of inactive cofactors 202 to active cofactors 204 may be controlled by photocatalysts. Photocatalysts are activated by light. Excitation of a photocatalyst will directly or indirectly change the oxidation state of the metal cofactors at the locations where the photocatalysts are activated. Location-specific control of photocatalysts may be achieved by using a photomask, digital micromirror device (DMD), or other type of optoelectronics to direct light onto only selected areas of the solid substrate 100.

A scavenger may also be present in the aqueous solution that covers the solid substrate 100. Scavengers prevent diffusion of metal cofactors in a state that catalyzes activity of a polymerase 102. Although the polymerases 102 are tethered to the surface of the solid substrate 100, the cofactors may diffuse and activate polymerases 102 at off-target locations such as, in this illustration, on the surface of the second electrode 108(B). Scavengers may change the oxidation state of an active cofactor 204 to that of an inactive cofactor 202. Scavengers can be oxidizers such as an amine in the presence of oxygen. Scavengers can be chelators such as EDTA and ethylenediamine that coordinate with and sequester metal cofactors without necessarily changing the oxidation state. Examples of scavengers, also called quench reagents, for divalent metal cations are provided in Michele Chiesi and Giuseppe Inesi, *The Use of Quench Reagents for Resolution of Single Transport Cycles in Sarcoplasmic Reticulum,* 254(20) J. Biol. Chem. 10370 (1979). The choice of scavenger depends on the metal cofactor and persons of ordinary skill in the art can select appropriate scavengers based on the type of metal cofactor and reaction conditions.

Extension of the polynucleotides 104 at locations on the solid substrate 100 where active cofactors 204, and active polymerases 102, are present is achieved by addition of nucleotides 112. The nucleotides 112 may be limited to a single species of nucleotide and provided across the entire surface of the solid substrate 100 as described in FIG. 1. However, unlike FIG. 1, the nucleotides 112 may or may not include blocking groups 106. The availability of nucleotides 112 and active polymerase 102 creates nucleotide extensions 114 on those areas of the solid substrate 100 where an electrode 108 was activated or a redox reagent was added.

If the polymerase 102 is a template-independent polymerase and the nucleotides 112 do not include blocking groups 106 more than one nucleotide 112 may be added during a given round of synthesis creating a homopolymer. The number of nucleotides 112 added to the polynucleotides 104 depends on the concentration of reagents and reaction conditions such as temperature and time. The number of nucleotides 112 may be controlled by adjusting the length of time that an electrode 108 is active and/or a concentration of the scavenger. Activating the electrode 108(A) for a shorter time results in shorter (or no) homopolymers and the length of homopolymers may increase as the length of time increases. Active cofactors 204 may be converted back to inactive cofactors 202 without the action of scavengers by reversing the redox process. Reversing the redox process for changes the voltage of an active electrode 108(A) can stop polymerization and may be used to control the length of homopolymer additions. Additionally, flooding the surface of the solid substrate with a wash solution will remove any free nucleotides 112 which also stops polymerization.

In FIG. 2 the nucleotides 112 are shown as being added after the inactive cofactors 202. However, in implementations, the nucleotides 112 and the inactive cofactors 202 may be added in the same reaction reagent solution.

This creates spatial addressability on the surface of the solid substrate 100 which allows for control of where nucleotides 112 are added to growing polynucleotides 104. In FIG. 2, nucleotide extension 114 is illustrated on the surface of one electrode 108(A). In subsequent rounds of extension, nucleotide extension 114 may occur at different areas such as on the surface of a different electrode 108(B). Repeated rounds of cofactor activation and extension by addition of a single species of nucleotide 112 allow for the synthesis of polynucleotides 104 with different and arbitrary sequences. Between each round, the active cofactors 204 and remaining nucleotides 112 may be removed by a wash step.

Figure 3:
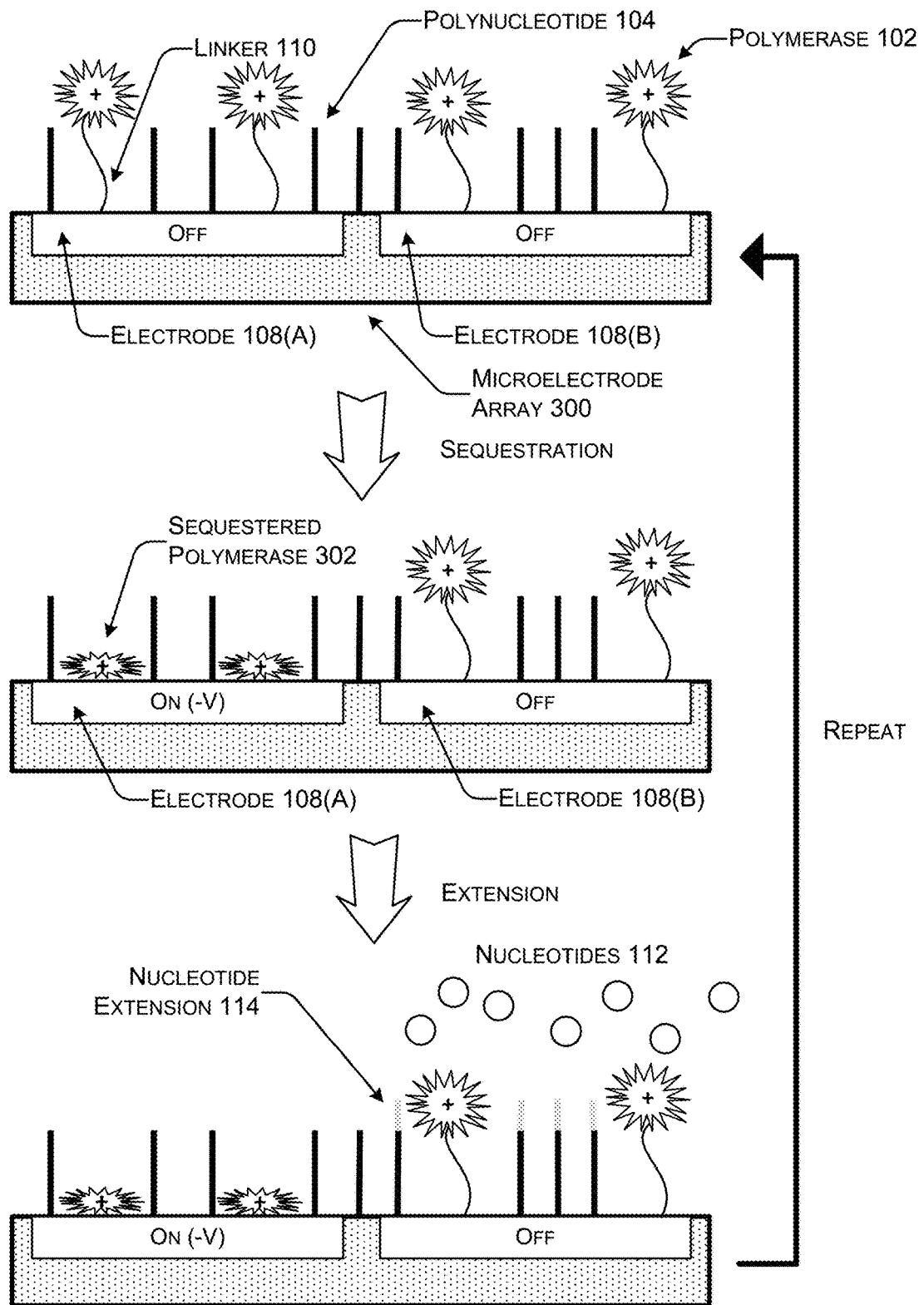
FIG. 3. is a diagram of polynucleotide synthesis with surface-bound polymerases on a microelectrode array in which spatial addressability is achieved by sequestering polymerases to the surface of the microelectrode array using electrostatic attraction to an activated electrode.

FIG. 3 shows spatial control of polymerase activity by electrostatic sequestration of polymerases 102 to the surface of a microelectrode array 300. Electrostatic sequestration uses electrical charge differences between a charged entity (e.g., a positively charged polymerase 102 or a negatively charged polynucleotide 104) and an electrode 108 to pull the charged entity toward the activated electrode. Without being bound by theory, it is believed that electrostatic sequestration can temporarily inactivate polymerases by removing the enzymes from solution so that they are unable to participate in reactions at an appreciable level and/or by changing the conformation of the enzyme so that activity is decreased or lost. With electrostatic sequestration, the solid substrate 100 is implemented as a microelectrode array 300. An aqueous solution covering the surface of the solid substrate 100 may include support electrolytes to transfer the charge from an electrode to the charged entity.

A polymerase 102 that is not naturally positively charged may be engineered to have a positive charge by replacing amino acids located on the outside of the enzyme's tertiary structure with amino acids that have positively charged side chains such as lysine, arginine, and/or histidine. Polynucleotides 104 naturally have negative charges due to negatively charged phosphate groups in the phosphodiester linkages.

Activation of an electrode 108(A) with a voltage having a charge that is opposite that of the charged entity prevents polymerization through electrostatic sequestration. FIG. 3 shows positively charged polymerases 102 sequestered on the surface of an electrode 108(A) when a negative voltage is applied to the electrode 108(A). This makes the polymerases 102 in proximity to the electrode 108(A) sequestered polymerases 302. Sequestered polymerases 302 are inactive because the attraction to the electrode 108(A) prevents the polymerases 102 from interacting with the anchored polynucleotides 104 or free nucleotides 112. Although not illustrated in FIG. 3, the polynucleotides 104 may be similarly attracted to an electrode 108 that is generating a positive voltage and inactivated through electrostatic sequestration.

In an implementation, the entity that is not being attracted to an electrode 108 (e.g., the polynucleotides 104 in FIG. 3) may be modified to have a neutral charge. This can prevent ion paring, for example, between a positively charged polymerase 102 and a negatively charged polynucleotide 104.

Activation of an electrode 108 to sequester polymerase 102 or polynucleotides 104 inhibits polymerization. Thus, polymerization only occurs at those areas on the microelectrode array 300 where electrodes 108 are not activated. This is shown by the nucleotide extension 114 on those polynucleotides 104 attached to the inactive electrode 108(B). This is the opposite of the effect of electrode activation that is shown in FIGS. 1 and 2. In FIG. 1, activation of an electrode 108(A) results in the removal of blocking groups 106 and promotes polymerization. In FIG. 2, activation of an electrode 108(A) results in conversion of an inactive cofactor 202 to an active cofactor 204 and promotes polymerization.

After sequestration, nucleotides 112 may be brought into contact with the surface of the microelectrode array 300. The nucleotides 112 may be limited to a single species of nucleotide and provided across the entire surface of the microelectrode array 300 as described in FIG. 1. The availability of nucleotides 112 and polymerase 102 creates nucleotide extensions 114 on those areas of the microelectrode array 300 where an electrode 108(B) is not active.

The nucleotides 112 may or may not include blocking groups 106. If the nucleotides 112 do not include blocking groups and the positively charged polymerase 102 is a template-independent polymerase, then homopolymers of multiple nucleotides 112 may be incorporated on the ends of the polynucleotides 104 during each round of synthesis. The number of nucleotides 112 added may be controlled by adjusting the length of time that the electrode 108(B) is turned off. Switching the electrode 108(B) off for a shorter time results in generally shorter (or no) homopolymer addition and the length of homopolymers increases as the time the electrode 108(B) is off increases.

As the cycle of sequestration and extension is repeated, different locations on the microelectrode array 300 are inactivated providing spatial control of the locations where nucleotides 112 are added to the polynucleotides 104. A selected nucleotide is provided each round which may be the same or a different nucleotide than was provided in a previous round. Between each round all electrodes 108 may be activated to prevent polymerization anywhere on the surface of the microelectrode array 300. A wash step between rounds may remove any remaining nucleotides 112.

Illustrative Process

For ease of understanding, the process discussed in this disclosure is delineated as separate operations represented as independent blocks. However, these separately delineated operations should not be construed as necessarily order dependent in their performance. The order in which the process is described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 4:
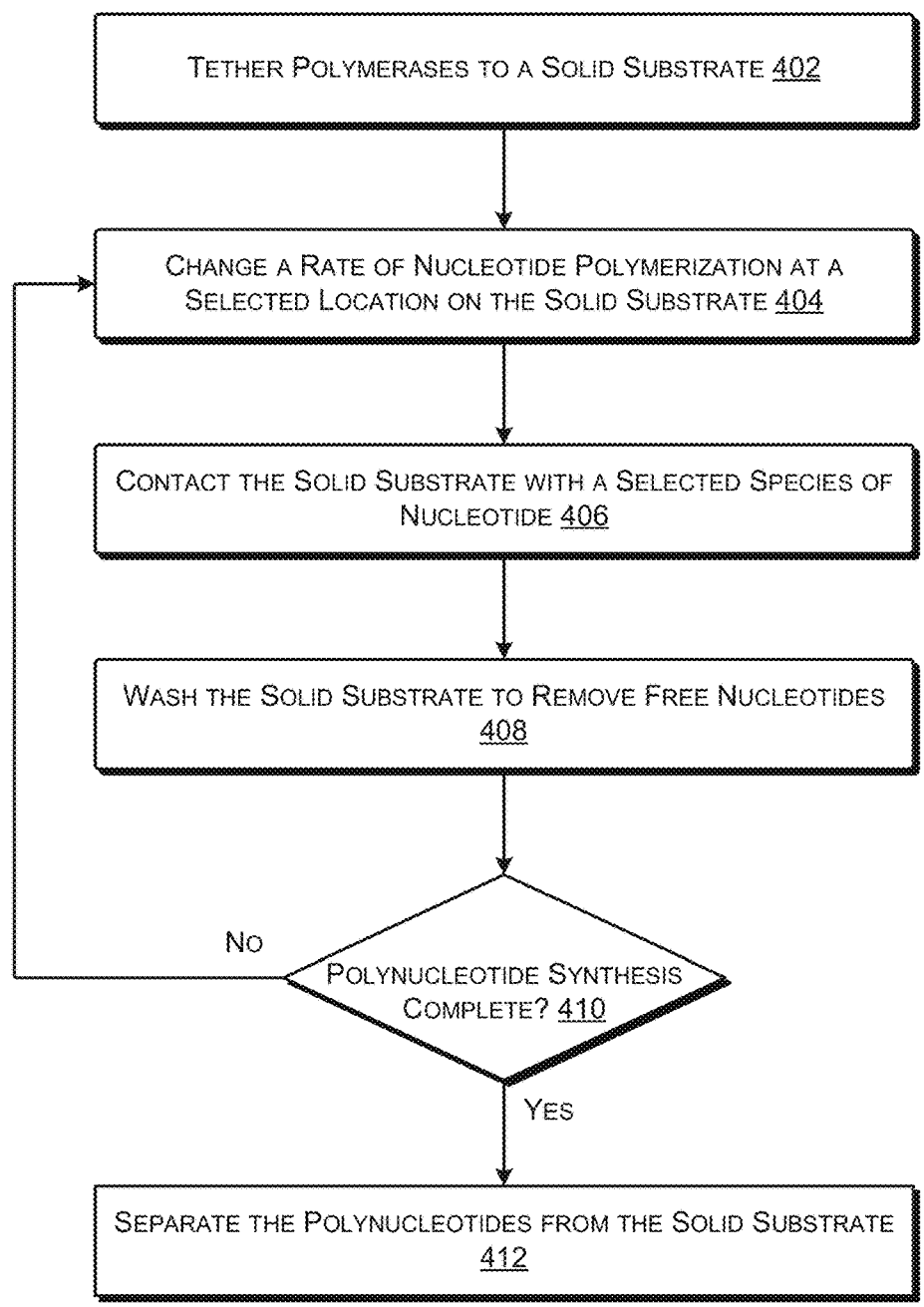
FIG. 4 is a flow diagram showing an illustrative process for de novo synthesis of polynucleotides using polymerases tethered to a solid substrate.

FIG. 4 shows process 400 for de novo synthesis of polynucleotides using polymerases tethered to a solid substrate. This process 400 may be implemented, for example, using any of the reactions, structures, and/or devices shown in FIGS. 1-3.

At operation 402, one or more polymerases are tethered to the surface of a solid substrate. All polymerases tethered to the solid substrate may be the same type of polymerase. The polymerases may be template-independent polymerases or template-dependent polymerases. The solid substrate may be made out of silicon dioxide, glass, an insoluble polymer, or other material. In an implementation, the solid substrate may be a microelectrode array. The polymerases may be directly attached to the solid substrate (or a functional coating on the solid substrate) by formation of a covalent bond with one or more molecules of the polymerases such as an amino acid side chain. The polymerases may be attached to the solid substrate (or a functional coating on the solid substrate) via a linker molecule. The solid substrate may be covered with many thousands or millions of separate polymerase enzymes.

At operation 404, a rate of nucleotide polymerization is changed at a selected location on the surface of the solid substrate. The nucleotide polymerization extends polynucleotides that are also attached to the surface of the solid substrate. The polynucleotides may be attached to the solid substrate by any known or later developed technique for anchoring single-stranded DNA or RNA to a solid support such as techniques used in conventional solid-phase synthesis of oligonucleotides or used for creation of DNA microarrays.

Changing the rate of nucleotide polymerization may be thought of as turning polymerization "on" or "off" Nucleotide polymerization may be promoted or "turned on" by causing a site-specific change at the selected location that increases the rate of nucleotide polymerization. Nucleotide polymerization may be inhibited or "turned off" by causing a site-specific change at the selected location that decreases the rate of nucleotide polymerization. The rate of polymerization may be decreased to zero or to a level that is insignificant and/or undetectable.

The selected location may be any one or more locations that are contiguous or separate on the surface of the solid substrate. The selected location may be a single spot, a group of spots located adjacent to each other, or multiple disparate spots spread across the surface of the array in any pattern.

Multiple different techniques may be used to change the rate of nucleotide polymerization at a selected location on the solid substrate. For example, the rate of nucleotide polymerization may be changed by selectively deblocking polynucleotides tethered to the surface of the solid substrate. Once deblocked, the polynucleotides can be extended by incorporation of nucleotides. The deblocking increases the rate of polymerization from zero or essentially zero.

The rate of nucleotide polymerization may also be changed by changing an oxidation state of a cofactor of the polymerases that are tethered to the solid substrate. When the cofactor is in an oxidation state that allows for ligand coordination the polymerase is active and can extend the polynucleotides attached to the solid substrate. Thus, change of the oxidation state of a cofactor increases the rate of polymerization if the cofactor is changed to an oxidation state that coordinates with the polymerase. The change decreases the rate of polymerization if the cofactor is changed to an oxidation state that does not coordinate with the polymerase.

The rate of nucleotide polymerization may also be changed by electrostatic sequestration of the polymerases or nucleotides on the surface of the microelectrode array. Polymerization is inhibited at the locations on the microelectrode array where the polymerases or the nucleotides are sequestered. Thus, electrostatic sequestration reduces the rate of polymerization.

The rate of nucleotide polymerization may also be changed by changing the pH of an aqueous solution in contact with the solid substrate. The rate of nucleotide polymerization may be decreased by changing the pH of the aqueous solution from a pH that is suitable for the polymerases to a pH that is not suitable. Alternatively, the rate of nucleotide polymerization may be increased by changing the pH of the aqueous solution from a pH that is not suitable for the polymerases to a pH that is suitable.

The selected location at which the rate of polymerization is changed (i.e., increased or decreased) may be controlled by many different mechanisms. If the solid substrate is implemented as a microelectrode array, activation of specific addressable electrodes can change the rate of polymerization. For example, activation of the microelectrode array can cleave electrochemically-cleavable blocking groups from the polynucleotides thereby increasing the rate of polymerization at those electrodes that are activated. Also, activation of the microelectrode array can change the oxidation state of a cofactor which may either increase or decrease the rate of polymerization.

Furthermore, activation of the microelectrode array can sequester polymerases or polynucleotides on the surface of the microelectrode array thereby decreasing the rate of polymerization at those electrodes that are activated. Also, activation of the microelectrode array can change the pH of the aqueous solution in contact with the microelectrode array by initiating a redox reaction at the selected location. This change in pH may increase or decrease the rate of polymerization depending on if the pH is changed to a range that is suitable for the polymerases or changed to a range this is not suitable.

Site-specific control of the rate of polymerization may also be achieved if the solid substrate is not a microelectrode array. In an implementation, target fluid deposition may be used to precisely apply a reagent to the selected location on the solid substrate. The reagent may be a deblocking agent or chemical cleavage agent that removes blocking groups and increase the rate of polymerization. The reagent may be a redox reagent that reduces or oxidizes the metal cofactor and either increases or decreases the rate of polymerization depending on the final oxidation state of the metal cofactor. The reagent may be an acid or base that changes the pH of an aqueous solution in contact with the solid substrate making the pH suitable (i.e., increasing the rate of polymerization) or not suitable (i.e., decreasing the rate of polymerization) for the polymerase.

In an implementation, a light source that is directed onto the selected location on the solid substrate by a photomask, DMD, or other optoelectronics may provide site-specific control of the rate of polymerization. The light source may cleave photolabile linkers releasing blocking groups and increasing the rate of polymerization. The light source may be used to change the oxidation state of metal cofactors by exciting a photocatalyst that performs a photoredox reaction with the metal cofactor or an intermediary. This may increase or decrease the rate of polymerization depending on the final oxidation state of the metal cofactor.

In an implementation, a heater can change the rate of polymerization at the selected location. The heater may raise the temperature at the surface of the solid substrate in an arbitrary and controllable pattern. The increased temperature can cleave thermolabile linkers and release blocking groups thereby increasing the rate of polymerization.

At operation 406, the solid substrate is contacted with a selected species of nucleotide. The nucleotides may include blocking groups that prevent incorporation of more than one nucleotide at a time. The nucleotides may lack blocking groups. A single species of nucleotide may be flooded in excess over the surface of the solid substrate. For example, the selected nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP). Selection of the nucleotide controls the base sequence of the polynucleotides that are synthesized on the solid substrate during this round of synthesis. In some implementations, the nucleotides may be added as part of the operation 404 that changes the rate of nucleotide polymerization.

At operation 408, the solid substrate is washed to remove free nucleotides. The wash solution may be flowed across the entire surface of the solid substrate displacing any remaining free nucleotides and any aqueous solution covering the solid substrate. This prevents incorporation of an incorrect nucleotide during a subsequent round of synthesis. Washing may stop polymerization by removal of nucleotides. The wash solution is water without added salts or an aqueous solution that contains at least one of a salt or a buffer. The buffer may be any one of a number of aqueous buffers that are compatible with polymerases and single-stranded nucleotides such as PBS or TBS. Because the polymerases are tethered to the solid substrate they are not removed by washing. Thus, the polymerases may be reused during subsequent rounds of nucleotide addition. The results in less waste and lower reagent costs than an implementation in which the polymerases are removed during each wash step.

At operation 410, it is determined if polynucleotide synthesis is complete. If all polynucleotides that are being synthesized on the surface of the solid substrate have reached their full lengths, synthesis is complete. Process 400 may then proceed along the "yes" path and end. If, however, polynucleotide synthesis is not yet complete, process 400 proceeds along "no" path and returns to operation 404 where the rate of nucleotide polymerization is changed at a different selected location on the solid substrate. This process may be repeated iteratively during synthesis of a batch of polynucleotides. During each round of synthesis, the selected nucleotide and the selected location may both be independently varied. This allows for the parallel synthesis of multiple polynucleotides each with a different sequence.

At operation 412, the polynucleotides may be separated from the solid substrate. If the polynucleotides are attached to the solid substrate by linkers, cleavage of the linkers may release the polynucleotides. Other techniques for separating polynucleotides from a solid substrate following solid-phase synthesis are known to those of ordinary skill in the art. Any suitable technique may be used. The polynucleotides may be collected and stored or processed further such as by amplification with polymerase chain reaction (PCR).

Illustrative Device and Computer Architecture

Figure 5:
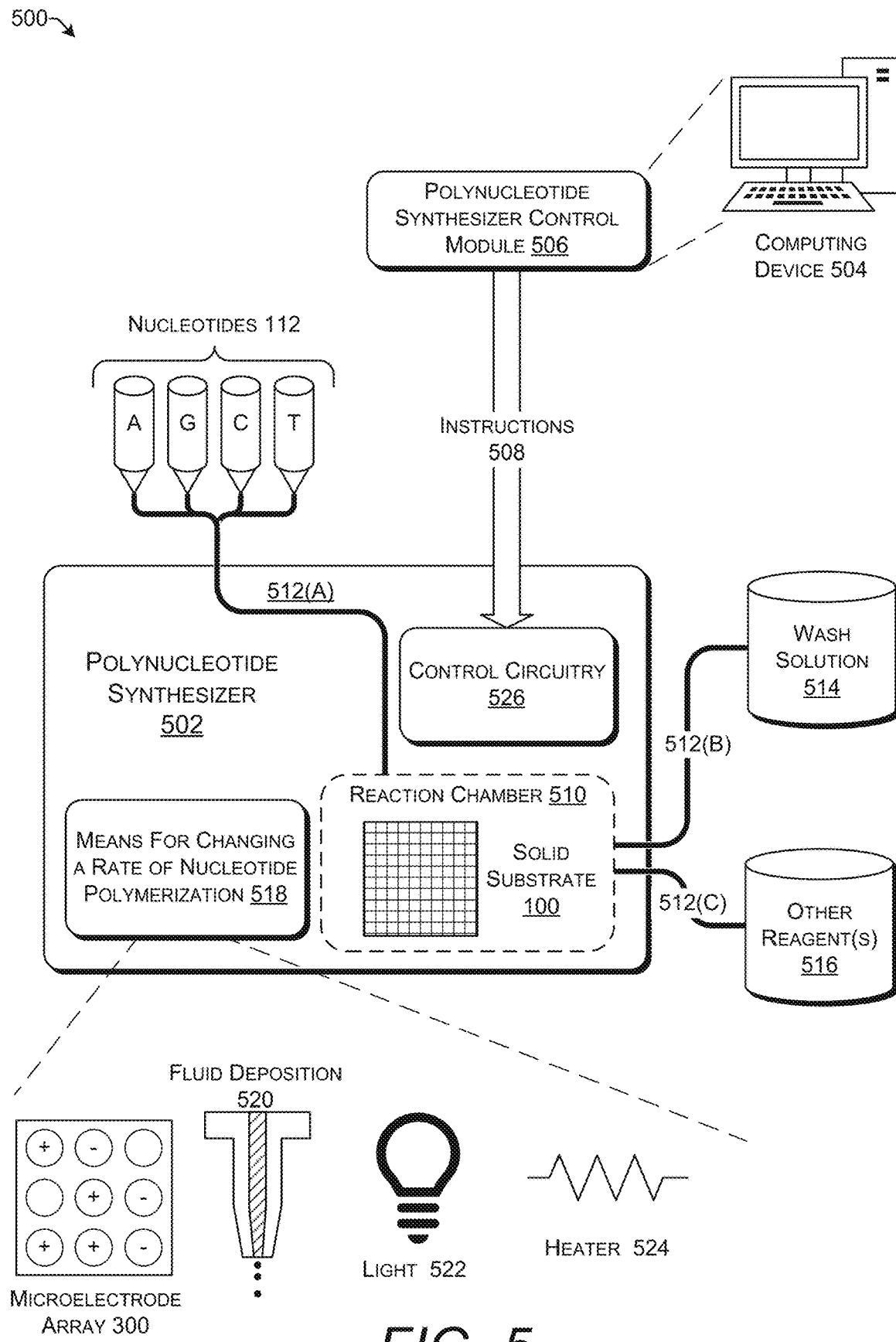
FIG. 5 is an illustrative device for synthesizing polynucleotides with polymerases bound to a solid substrate.

FIG. 5 is an illustrative architecture 500 of a device for implementing aspects of this disclosure. The architecture 500 includes a polynucleotide synthesizer 502 and may also include a computing device 504. The computing device 504 includes a polynucleotide synthesizer control module 506. The polynucleotide synthesizer control module 506 provides instructions 508 that can control operation of the polynucleotide synthesizer 502. For example, the instructions 508 may communicate to the polynucleotide synthesizer 502 base sequences of polynucleotides 104 for synthesis. The computing device 504 may be implemented as any type of conventional computing device such as a desktop computer, a laptop computer, a server, a hand-held device, or the like. In an implementation, the computing device 504 may be a part of the polynucleotide synthesizer 502 rather than a separate device.

The polynucleotide synthesizer 502 is a device that performs automated solid-phase synthesis of polynucleotides 104 on a solid substrate 100. The solid substrate 100 may be located within a reaction chamber reaction 510 that can contain an aqueous solution such as a reaction reagent solution in contact with the surface of the solid substrate 100.

The solid substrate 100 may an array or other structure with a substantially flat two-dimensional structure on which nucleotide polymerization occurs. The solid substrate 100 may be formed from silicon dioxide, glass, an insoluble polymer, a non-reactive metal such as gold, silver, or platinum, or other material. The solid substrate 100 may be an electrochemically inert surface or it may include an array of spatially addressable microelectrodes. Thus, in an implementation, the solid substrate 100 may be a microelectrode array.

The polynucleotide synthesizer 502 may also include storage tanks, bottles, vials, or other containers or receptacles for storing nucleotides 112. A selected one of the nucleotides 112 may be brought into contact with the solid substrate 100 through a fluid delivery pathway 512(A). The fluid delivery pathway 512(A), and all fluid delivery pathways 512 generally, may be implemented by tubes and pumps, microfluidics, laboratory robotics, or other techniques. If synthesizing DNA, for example, the nucleotides 112 may be dNTPs that include one of the natural bases adenine (A), guanine (G), cytosine (C), or thymine (T). In some implementations, the nucleotides 112 may include blocking groups 106. Although four different types of nucleotides 112 are illustrated in FIG. 5, the polynucleotide synthesizer 502 may include fewer types (e.g., omit one of the standard nucleotides) or more types (e.g., include one or more artificial bases). Only one type of selected nucleotide is provided during each round of synthesis to control which nucleotide is next incorporated by the polymerase 102 into the polynucleotides 104. However, during rounds of synthesis different ones of the available nucleotides 112 may be introduced to create a plurality of polynucleotides 104 each with a different nucleotide sequence.

The nucleotides 112 may be provided in a reaction reagent solution. The reaction reagent solution is an aqueous solution that contains a selected one of the nucleotides 112 and at least one of a salt or buffer. The reaction reagent solution may also include a metal cofactor for the polymerase 102. The metal cofactor may be provided in the inactive oxidation state or the active oxidation state.

The buffer may be any one of a number of aqueous buffers that are compatible with the polymerase 102 such as, for example, phosphate-buffered saline (PBS). PBS is a water-based salt solution containing disodium hydrogen phosphate, sodium chloride and, in some formulations, may also include one or more of potassium chloride and potassium dihydrogen phosphate. Other examples of aqueous buffers known to those of ordinary skill in the art include HEPES, MOPS, PBS, PBST, TAE, TBE, TBST, TE, and TEN. See Vincent S. Stoll & John S. Blanchard, *Buffers: Principles and Practice,* 182 Meth. Enzoml., 24 (1990).

The polynucleotide synthesizer 502 may also include a wash solution 514. The wash solution 514 may be water (e.g., DI (deionized) water) or an aqueous solution that contains at least one of a salt or a buffer. The salt or the buffer may be the same as the salt or buffer used in the reaction reagent solution. The wash solution 514 is flowed into the reaction chamber 510 through a fluid delivery pathway 512(B). The wash solution 514 is used to remove the reaction free nucleotides 112 and possible other reagents from the reaction chamber 510. By removal of free nucleotides 112, the next round of polymerization may occur with a different nucleotide 112 without contamination from the previous round (although multiple rounds of addition of the same nucleotide 112 are possible).

One or more other reagents 516 may also be included in the polynucleotide synthesizer 502 and brought into contact with the solid substrate 100 though a fluid delivery pathway 512(B). If multiple other reagents 516 are available, each may be delivered through a separate fluid delivery pathway 512(B) or two or more of the other reagents 516 may share at least in part the same fluid delivery pathway 512(B). The other reagents 516 may include, for example, a chemical cleavage agent, a deblocking agent, a redox reagent, a support electrolyte, a metal cofactor, and/or a scavenger.

As discussed above, there are multiple different devices and techniques for controlling the spatial location of polymerization on the surface of the solid substrate 100. All of these different devices and techniques are referred to collectively as a means for changing a rate of nucleotide polymerization 518. The rate of polymerization for extension of the polynucleotides 104 tethered to the surface of the solid substrate 100 is changed at selected locations on the surface of the solid substrate 100. Polymerization is promoted by increasing the rate of nucleotide polymerization from zero or a negligible level to a level at which the polymerase 102 can act at a rate that is the same or similar to polymerase activity in conventional enzymatic DNA synthesis. This may be thought of as "activating" polymerization. Polymerization is inhibited by reducing the rate of nucleotide polymerization to zero or a negligible level. This may be thought of as "deactivating" polymerization. The spatial pattern of control of the rate of nucleotide polymerization causes location-specific polymerization. The means for changing the rate of nucleotide polymerization 518 may be any of a microelectrode array 300, (e.g., the solid substrate 100 is or includes a microelectrode array), a target fluid deposition instrument 520, a light source 522, or a heater 524.

The means for changing the rate of nucleotide polymerization 518 may be controlled by control circuitry 526. The control circuitry 526 may be implemented as any type of circuitry suitable for controlling hardware devices such as a printed circuit board, microcontroller, a programmable logic controller (PLC), or the like. The control circuitry 526 receives and acts on the instructions 508 provided by the polynucleotide synthesizer control module 506. Thus, the control circuitry 526, through the means for changing the rate of nucleotide polymerization 518, can control where polymerization occurs on the surface of the solid substrate 100. The control circuitry 526 may also control the fluid delivery pathways 512. Thus, the control circuitry 526 can control where polymerization occurs and the species of nucleotide that is added during any round of synthesis.

If the means for changing the rate of nucleotide polymerization 518 is a microelectrode array 300, the control circuitry 526 may be able to set the voltage independently at any (or all) of the electrodes in the microelectrode array in any arbitrary pattern. The microelectrode array 300 may be any of the microelectrode arrays described in this disclosure. In an implementation, the microelectrode array 300 may be used to remove blocking groups 106 from the polynucleotides 104. In an implementation, the microelectrode array 300 may be used to change the activation state of metal cofactors for the polymerase 102. In an implementation, the microelectrode array 300 may be used to cause a redox reaction that changes the pH to a range that is unsuitable or suitable for the polymerase 102 thereby inactivating or activating the polymerase 102. In an implementation, the microelectrode array 300 may be used to electrostatically sequester positively charged polymerases 102 or polynucleotides 104 to the surface of the microelectrode array 300.

If the means for changing the rate of nucleotide polymerization 518 is an target fluid deposition instrument 520, the control circuitry 526 may control the location of a print nozzle and the type of reagent that is dispensed. Thus, the control circuitry 526 may cause a deblocking agent, a linker cleavage agent, a chemical redox reagent, etc. to be dispensed according to any arbitrary pattern across one or more selected locations on the surface of the solid substrate 100. The target fluid deposition instrument 520 may be implemented as any type of equipment or device such as a chemical inkjet printing device or precision laboratory robotics that can precisely apply small volumes of chemical reagents to specific locations on the surface of the solid substrate 100. Chemical inkjet printing uses techniques similar to conventional printing to place nanoliter volumes of reagents at specified locations on a two-dimensional surface. Techniques for using inkjet printing to precisely deliver chemical reagents to selected locations on a surface of an array are well-known to those of ordinary skill in the art. See Paul Calvert, *Inkjet Printing for Materials and Devices,* 13(10) Chem. Mater. 3299 (2001).

Any type of chemical inkjet printing may be adapted for use with this disclosure. Inkjet printing can be divided into two categories: (1) drop-on-demand (DoD) or impulse inkjet, where droplets are generated when required; and (2) continuous inkjet, in which droplets are deflected from a continuous stream to a substrate when needed. Inkjet printing can be further subdivided according to the specific means of generating droplets, such as piezoelectric, thermal, and electrostatic. Droplet size involves, typically, volumes ranging from 1.5 pL to 5 nL at a rate of 0-25 kHz for drop-on-demand printers (and up to 1 MHz for continuous printheads).

Electrohydrodynamic jet printing (EHJP) is another printing technology that may be used. EHJP is a high-resolution printing technology where the printed liquid is driven by an electric field. Exposure to an electric field causes mobile ions in a polarizable liquid to accumulate at the liquid surface. Deposited droplets can be as small as 240 nm with spatial accuracy in the hundreds of nm, which is typically an order of magnitude smaller than other inkjet printing technologies. Such small droplet sizes dispense less material with more spatial control, which allows for more selectivity in controlling the removal of blocking groups 106.

In this implementation, the solid substrate 100 does not need to contain electrodes and may be an electrochemically inert surface. In an implementation, the target fluid deposition instrument 520 may deliver a chemical cleavage agent that removes a blocking group 106. The chemical cleavage agent may be an acid or a base that cleaves acid-liable or base-liable linkers. In an implementation, the chemical reagent delivered by the target fluid deposition instrument 520 may be a redox reagent which is a reducing reagent or oxidizing reagent that changes the oxidation state of the metal cofactor. For example, the chemical redox reagent may be ascorbic acid or an amine such as ammonia.

Addition of acid or base by the target fluid deposition instrument 520 may also be used to inactivate or activate the polymerases by changing the local pH to a range that is unsuitable or suitable for the enzymes. If the aqueous solution that contacts the surface of the solid substrate 100 is buffered to a pH that is suitable for the type of polymerase tethered to the solid substrate 100, raising or lowering the pH sufficient can denature the polymerase and decrease or stop its activity. Alternatively, the aqueous solution that contacts the surface of the solid substrate 100 may be buffed to a pH that is not suitable for the polymerase. Addition of an acid or base that moves the pH into a range suitable for the polymerase will activate the polymerase and enable polymerization to occur at those locations where the target fluid deposition instrument 520 added the acid or base. The buffering capacity of the aqueous solution controls the range over which the added acid or base can affect pH. As the buffering capacity increases the area of effect is decreased and spatial control is more precise.

If the means for changing the rate of nucleotide polymerization 518 is a light source 522, the control circuitry 526 may turn the light source on and off and control where light from the light source 522 contacts the solid substrate 100. Light from the light source 522 may be directed or focused by the control circuitry 526 on to the surface of the solid substrate 100 by optoelectronics such as a photomask or digital micromirror device (DMD). One example of a DMD that directs light onto an array surface is provided in Howon Lee et al. supra. The light source 522 generates light of a specific wavelength or range of wavelengths. Light from the light source 522 may be used to cleave a photolabile linker or remove a photolabile blocking group 106.

Photolabile linkers are cleaved by a specific wavelength of light corresponding to the linker chemistry. There are a large number of known types of photo-cleavable bonds. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain. Amine-to-thiol bonds may be cleaved by ultraviolet (UV) light with a wavelength of about 365-405 nm. The list of functional groups that can be protected include, but are not limited to, phosphates, carboxylates, carbonates, carbamates, thiolates, phenolates, and alkoxides.

One type of photolabile linker uses a UV photo-cleavable C3 spacer arm that includes a nitrobenzene sidechain. Cleavage occurs by irradiation with UV light (300-350 nm). Other examples of photolabile linkers are PC Biotin Phosphoramidite with the formula 1-[2-Nitro-5-(6-(N-(4,4'-dimethoxytrityl))-biotinamidocaproamidomethyl)phenyl]-ethyl-[2-cyanoethyl-(N,N-diisopropyl)]-phosphoramidite, PC Amino-Modifier Phosphoramidite with the formula [(6-Trifluoroacetylami docaproamidomethyl)-1-(2-nitrophenyl)-ethyl]-2-cyanoethyl-(N,N-diisopropyl)-phosphoramidite, PC Spacer Phosphoramidite with the formula [4-(4,4'-Dimethoxytrityloxy)butyramidomethyl)-1-(2-nitrophenyl)-ethyl]-2-cyanoethyl-(N,N-diisopropyl)-phosphoramidite, and PC Linker Phosphoramidite with the formula 3-(4,4'-Dimethoxytrityl)-1-(2-nitrophenyl)-propan-1-yl-[(2-cyanoethyl)-(N,N-diisopropyl)]-phosphoramiditen (available from Glen Research, Sterling, Va.).

Light from the light source 522 may also be used to change the oxidation state of metal cofactors. Light from the light source 522 can excite a photocatalyst that performs a photoredox reaction with the metal cofactor or an intermediary. The light may be of any spectrum that is capable of initiating a photochemical reaction that does not damage the polynucleotides 104 or the polymerase 102. In an implementation, the light source 522 generates visible light. One suitable class of photoredox catalyst is the metal polypyridyl complexes of which iridium polypyridyl complexes are one example. These types of photoredox catalysts can perform single electron transfers (SET) as part of a series of reactions that reduce Co(III) to Co(II). See Megan H. Shaw et al., *Photoredox Catalysis in Organic Chemistry*, 81 J. Org. Chem. 5898 (2016).

If the means for changing the rate of nucleotide polymerization 518 is a heater 524, the control circuitry 526 may control the temperature and the locations on the solid substrate 100 that are heated. The control circuitry 526 may be able to create any arbitrary pattern of heated and non-heated locations on the surface of the solid substrate 100. The heater 524 may be used to cleave thermolabile linkers and release blocking groups 106. In an implementation, heat may be created by resistors. Electrodes in the microelectrode array may be coupled to localized heat sources such as spatially-addressable resistors. Heat created by the resistor can cleave thermally-labile linkers within sufficient proximity to the resistor that the temperature of the linker rises above its cleavage temperature. Heat may be generated by heat sources other than resistors. For example, lasers or focused ultrasound beams may be used to heat specific regions on the surface of the solid substrate 100.

Figure 6:
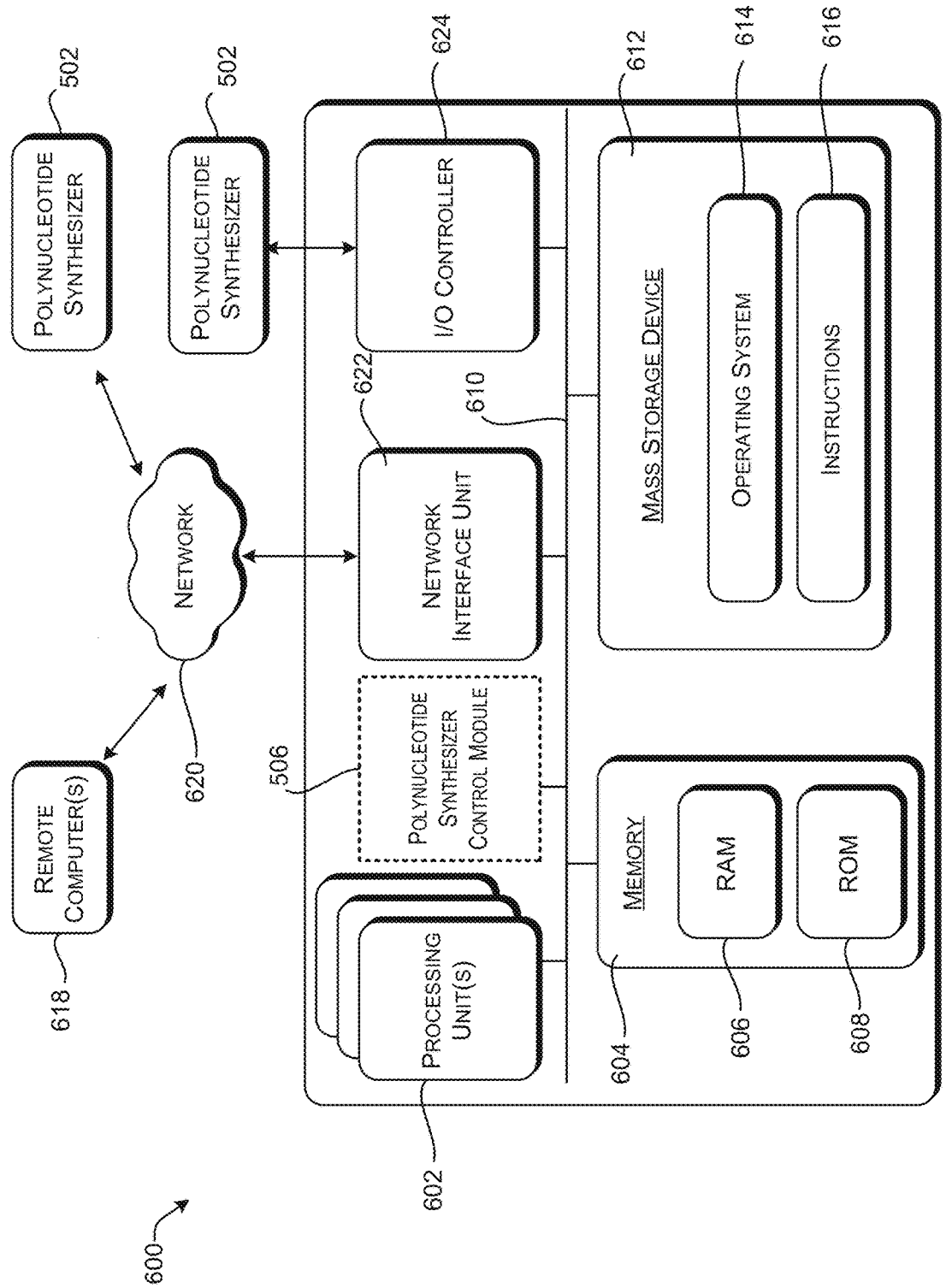
FIG. 6 is an illustrative computer architecture for implementing techniques of this disclosure.

FIG. 6 is a computer architecture diagram showing an illustrative computer hardware and software architecture for a computing device such as the computing device 504 introduced FIG. 5. In particular, the computer 600 illustrated in FIG. 6 can be utilized to implement the polynucleotide synthesizer control module 506.

The computer 600 includes one or more processing units 602, a memory 604, that may include a random-access memory 606 ("RAM") and a read-only memory ("ROM") 608, and a system bus 610 that couples the memory 604 to the processing unit(s) 602. A basic input/output system ("BIOS" or "firmware") containing the basic routines that help to transfer information between elements within the computer 600, such as during startup, can be stored in the ROM 608. The computer 600 further includes a mass storage device 612 for storing an operating system 614 and other instructions 616 that represent application programs and/or other types of programs such as, for example, instructions to implement the polynucleotide synthesizer control module 506. The mass storage device 612 can also be configured to store files, documents, and data such as, for example, sequence data that is provided to the polynucleotide synthesizer 502 in the form of instructions 508.

The mass storage device 612 is connected to the processing unit(s) 602 through a mass storage controller (not shown) connected to the bus 610. The mass storage device 612 and its associated computer-readable media provide non-volatile storage for the computer 600. Although the description of computer-readable media contained herein refers to a mass storage device, such as a hard disk, solid-state drive, CD-ROM drive, DVD-ROM drive, or USB storage key, it should be appreciated by those skilled in the art that computer-readable media can be any available computer-readable storage media or communication media that can be accessed by the computer 600.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 606, ROM 608, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 600. For purposes of the claims, the phrase "computer-readable storage medium," and variations thereof, does not include waves or signals per se or communication media.

According to various configurations, the computer 600 can operate in a networked environment using logical connections to a remote computer(s) 618 through a network 620. The computer 600 can connect to the network 620 through a network interface unit 622 connected to the bus 610. It should be appreciated that the network interface unit 622 can also be utilized to connect to other types of networks and remote computer systems. The computer 600 can also include an input/output (I/O) controller 624 for receiving and processing input from a number of other devices, including a keyboard, mouse, touch input, an electronic stylus (not shown), or equipment such as a polynucleotide synthesizer 502 for synthesizing polynucleotides according to the techniques of this disclosure. Similarly, the input/output controller 624 can provide output to a display screen or other type of output device (not shown).

It should be appreciated that the software components described herein, when loaded into the processing unit(s) 602 and executed, can transform the processing unit(s) 602 and the overall computer 600 from a general-purpose computing device into a special-purpose computing device customized to facilitate the functionality presented herein. The processing unit(s) 602 can be constructed from any number of transistors or other discrete circuit elements, which can individually or collectively assume any number of states. More specifically, the processing unit(s) 602 can operate as a finite-state machine, in response to executable instructions contained within the software modules disclosed herein. These computer-executable instructions can transform the processing unit(s) 602 by specifying how the processing unit(s) 602 transitions between states, thereby transforming the transistors or other discrete hardware elements constituting the processing unit(s) 602.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 600 to store and execute the software components presented herein. It also should be appreciated that the architecture shown in FIG. 6 for the computer 600, or a similar architecture, can be utilized to implement many types of computing devices such as desktop computers, notebook computers, servers, supercomputers, gaming devices, tablet computers, and other types of computing devices known to those skilled in the art. For example, the computer 600 may be wholly or partially integrated into the polynucleotide synthesizer 502. It is also contemplated that the computer 600 might not include all of the components shown in FIG. 6, can include other components that are not explicitly shown in FIG. 6, or can utilize an architecture different than that shown in FIG. 6.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A solid substrate (100) having polymerases (102) and polynucleotides (104) tethered to the surface.

Clause 2. The solid substrate of clause 1, wherein the solid substrate comprises a microelectrode array.

Clause 3. The solid substrate of any of clauses 1-2, wherein the microelectrode array comprises a CMOS array.

Clause 4. The solid substrate of any of clause 2-3, wherein the polymerases are modified to have positive or neutral charges.

Clause 5. The solid substrate of any of clauses 1-4, wherein the polymerases are template-independent polymerases.

Clause 6. The solid substrate of any of clauses 1-5, wherein the polymerases are tethered to the surface by a linker.

Clause 7. The solid substrate of any of clauses 1-6, wherein the polynucleotides comprise 3' blocking groups.

Clause 8. The solid substrate of clause 7, wherein the solid substrate comprises a microelectrode array and wherein the 3' blocking groups are electrochemically cleavable by activity of an electrode of the microelectrode array.

Clause 9. A method of using polymerases (102) tethered to a solid substrate (100) for solid-phase polynucleotide synthesis, the method comprising: changing a rate of nucleotide polymerization that extends polynucleotides (104) tethered to the surface of the solid substrate (100) at a selected location on the surface of the solid substrate (100); contacting the solid substrate (100) with a selected species of nucleotide (112); washing the solid substrate to remove free nucleotide (112); and iteratively repeating steps a-c.

Clause 10. The method of clause 9, wherein during iterations of repeating steps a-c the selected location changes at least once Clause 11. The method of any of clauses 9-10, wherein during iterations of repeating steps a-c the selected species of nucleotide changes at least once.

Clause 12. The method of any of clauses 9-11, wherein the selected location and the selected species of nucleotide both change at least once.

Clause 13. The method of any of clauses 9-12, wherein changing the rate of nucleotide polymerization comprises selectively deblocking polynucleotides tethered to the surface of the solid substrate at the selected location.

Clause 14. The method of clause 13, wherein the selectively deblocking comprises removing a blocking group from the 3' end of the polynucleotides by a change in concentration of a chemical reagent, light, temperature, or pH.

Clause 15. The method of any of clauses 9-14, wherein the solid substrate comprises a microelectrode array.

Clause 16. The method of clause 15, wherein changing the rate of nucleotide polymerization comprises selectively deblocking polynucleotides tethered to the surface of the solid substrate at the selected location by cleaving electrochemically-cleavable blocking groups through activation of the microelectrode array.

Clause 17. The method of clause 15, wherein changing the rate of nucleotide polymerization comprises changing an oxidation state of a cofactor of the polymerase through activation of the microelectrode array.

Clause 18. The method of clause 15, wherein changing the rate of nucleotide polymerization comprises electrostatic sequestration of the polymerases or of the polynucleotides on the surface of the microelectrode array.

Clause 19. The method of clause 15, wherein changing the rate of nucleotide polymerization comprises changing the pH of an aqueous solution in contact with the microelectrode array by a redox reaction initiated by activation of the microelectrode array at the selected location.

Clause 20. The method of any of clauses 9-19, further comprising tethering the polymerases to the surface of the solid substrate.

Clause 21. The method of any of clauses 9-20, further comprising separating the polynucleotides from the surface of the solid substrate.

Clause 22. A device (502) for de novo synthesis of polynucleotides, the device comprising: solid substrate (100) having polymerases (102) and polynucleotides (104) tethered to the surface; means for changing a rate of nucleotide polymerization (518) at a selected location on the surface of the solid substrate (100); a fluid delivery pathway (512(A)) configured to contact the solid substrate with a selected nucleotide; and control circuity (526) configured to change the selected location and activate the fluid delivery pathway (512(A)).

Clause 23. The device of clause 22, wherein the means for changing the rate of nucleotide polymerization comprises a microelectrode array.

Clause 24. The device of clause 22, wherein the means for changing the rate of nucleotide polymerization comprises a targeted fluid deposition instrument, a light source, or a heater.

Clause 25. The device of any of clauses 22-24, wherein the polymerase comprises a template-independent polymerase.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A solid substrate having polymerases and polynucleotides tethered to a surface, wherein:
the solid substrate comprises a microelectrode array, or
the polymerases are tethered to the surface by a linker.

2. The solid substrate of claim 1, wherein the polynucleotides comprise 3' blocking groups.

3. The solid substrate of claim 1, wherein the solid substrate comprises a microelectrode array and the polymerases are modified to have positive or neutral charges.

4. The solid substrate of claim 1, wherein the polymerases are template-independent polymerases.

5. A solid substrate having polymerases and polynucleotides tethered to a surface of the solid substrate, wherein the polynucleotides comprise 3' blocking groups.

6. The solid substrate of claim 5, wherein the polymerases are tethered to the surface by a linker.

7. The solid substrate of claim 5, wherein the solid substrate comprises a microelectrode array and wherein the 3' blocking groups are electrochemically cleavable by activity of an electrode of the microelectrode array.

8. A method of using polymerases tethered to a solid substrate for solid-phase polynucleotide synthesis, the method comprising:
 a. changing a rate of nucleotide polymerization that extends polynucleotides tethered to the surface of the solid substrate at a selected location on the surface of the solid substrate;
 b. contacting the solid substrate with a selected species of nucleotide;
 c. washing the solid substrate to remove free nucleotide; and
 d. iteratively repeating steps a-c.

9. The method of claim 8, wherein during iterations of repeating steps a-c the selected location or the selected species of nucleotide change at least once.

10. The method of claim 8, wherein changing the rate of nucleotide polymerization comprises selectively deblocking polynucleotides tethered to the surface of the solid substrate at the selected location.

11. The method of claim 10, wherein the selectively deblocking comprises removing a blocking group from the 3' end of the polynucleotides by a change in concentration of a chemical reagent, light, temperature, or pH.

12. The method of claim 8, wherein the solid substrate comprises a microelectrode array.

13. The method of claim 12, wherein changing the rate of nucleotide polymerization comprises selectively deblocking polynucleotides tethered to the surface of the solid substrate at the selected location by cleaving electrochemically-cleavable blocking groups through activation of the microelectrode array.

14. The method of claim 12, wherein changing the rate of nucleotide polymerization comprises changing an oxidation state of a cofactor of the polymerase through activation of the microelectrode array.

15. The method of claim 12, wherein changing the rate of nucleotide polymerization comprises electrostatic sequestration of the polymerases or of the polynucleotides on the surface of the microelectrode array.

16. The method of claim 12, wherein changing the rate of nucleotide polymerization comprises changing the pH of an aqueous solution in contact with the microelectrode array by a redox reaction initiated by activation of the microelectrode array at the selected location.

17. The method of claim 8, further comprising tethering the polymerases to the surface of the solid substrate.

18. A device for de novo synthesis of polynucleotides, the device comprising:
 a solid substrate having polymerases and polynucleotides tethered to the surface;
 means for changing a rate of nucleotide polymerization at a selected location on the surface of the solid substrate;
 a fluid delivery pathway configured to contact the solid substrate with a selected nucleotide; and
 control circuitry configured to change the selected location and activate the fluid delivery pathway.

19. The device of claim 18, wherein the means for changing the rate of nucleotide polymerization comprises a microelectrode array.

20. The device of claim 18, wherein the means for changing the rate of nucleotide polymerization comprises a targeted fluid deposition instrument, a light source, or a heater.

* * * * *